United States Patent [19]
Hofmann et al.

[11] Patent Number: 6,055,453
[45] Date of Patent: Apr. 25, 2000

[54] APPARATUS FOR ADDRESSING NEEDLE ARRAY ELECTRODES FOR ELECTROPORATION THERAPY

[75] Inventors: Gunter A. Hofmann; Sukhendu B. Dev, both of San Diego; Steven C. Dimmer, Valley Center; Jeffrey I. Levatter, Rancho Santa Fe; Gurvinder S. Nanda, San Diego, all of Calif.

[73] Assignee: Genetronics, Inc., San Diego, Calif.

[21] Appl. No.: 08/905,240

[22] Filed: Aug. 1, 1997

[51] Int. Cl.$^7$ ....................................................... A61N 1/30
[52] U.S. Cl. ................................................. 604/21; 607/116
[58] Field of Search ............................ 604/890.1, 19–22, 604/500, 501; 128/898; 607/2, 100, 116, 154, 148, 115; 435/173.5, 173.6; 326/37

[56] References Cited

U.S. PATENT DOCUMENTS

| | | | |
|---|---|---|---|
| 4,931,046 | 6/1990 | Newman | 604/20 |
| 5,019,034 | 5/1991 | Weaver et al. | 604/890.1 |
| 5,273,525 | 12/1993 | Hofmann . | |
| 5,389,069 | 2/1995 | Weaver . | |
| 5,439,440 | 8/1995 | Hofmann | 604/49 |
| 5,468,223 | 11/1995 | Mir | 604/51 |
| 5,545,130 | 8/1996 | Hofmann et al. | 935/52 |
| 5,645,526 | 7/1997 | Flower | 604/20 |
| 5,674,267 | 10/1997 | Mir et al. | 607/72 |
| 5,688,232 | 11/1997 | Flower | 604/20 |
| 5,688,233 | 11/1997 | Hofmann et al. | 607/149 |
| 5,702,359 | 12/1997 | Hormann et al. | 604/20 |
| 5,800,378 | 9/1998 | Edwards et al. . | |
| 5,810,762 | 9/1998 | Hofmann | 607/145 |

*Primary Examiner*—Wynn Wood Coggins
*Assistant Examiner*—Sharon Finkel
*Attorney, Agent, or Firm*—Gray, Cary, Ware & Freidenrich, LLP; Lisa A. Haile

[57] ABSTRACT

A method and apparatus for in vivo electroporation therapy. Using electroporation therapy (EPT) as described in the invention, tumors treated by a combination of electroporation using the apparatus of the invention and a chemotherapeutic agent caused regression of tumors in vivo. In one embodiment, the invention provides a method of EPT utilizing low voltage and long pulse length for inducing cell death. One embodiment of the invention includes a system for clinical electroporation that includes a needle array electrode having a "keying" element that determines the set point of the therapy voltage pulse and/or selectable array switching patterns. A number of electrode applicator designs permit access to and treatment of a variety of tissue sites. Another embodiment provides a laparoscopic needle applicator that is preferably combined with an endoscope for minimally invasive EPT.

28 Claims, 17 Drawing Sheets

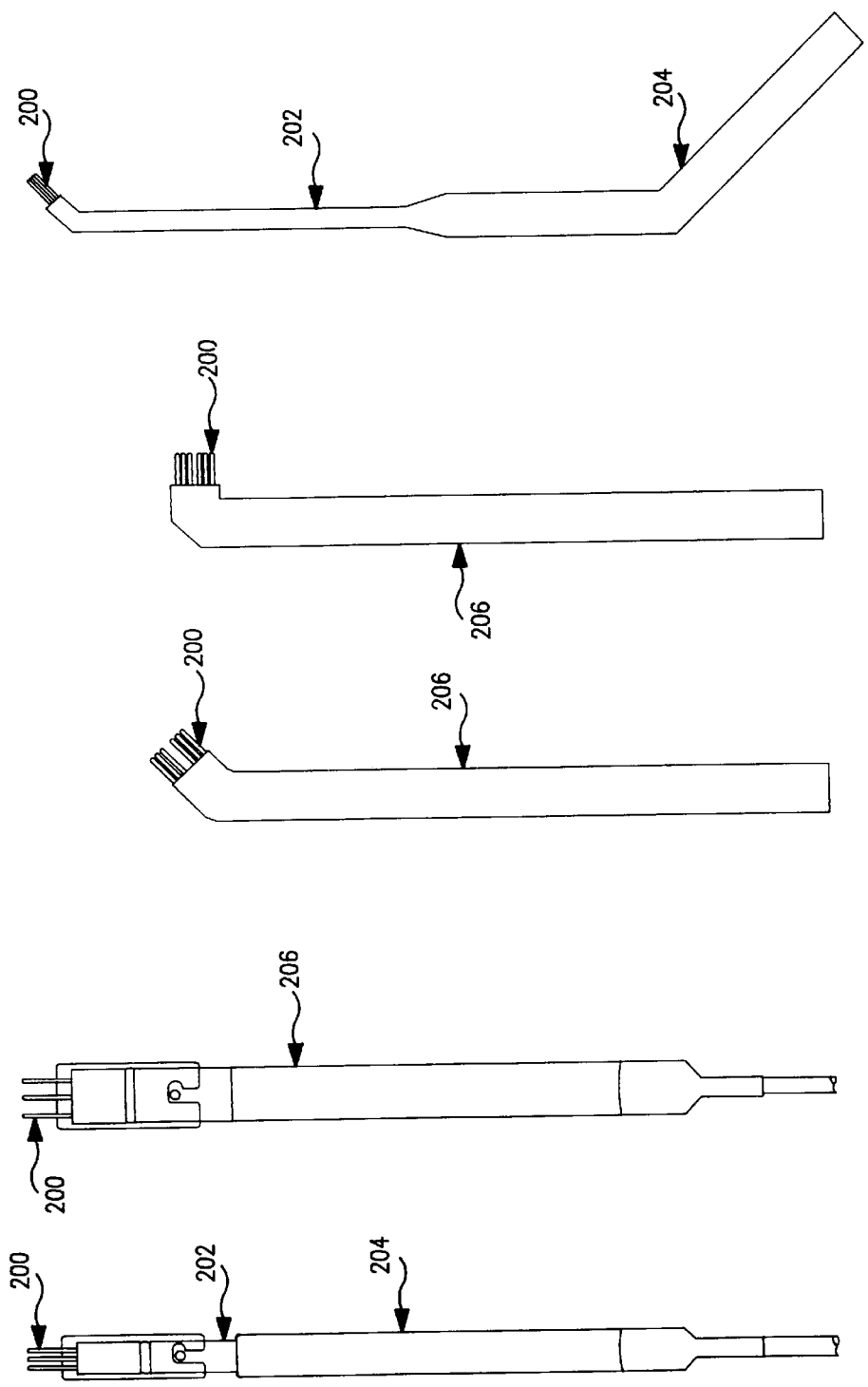

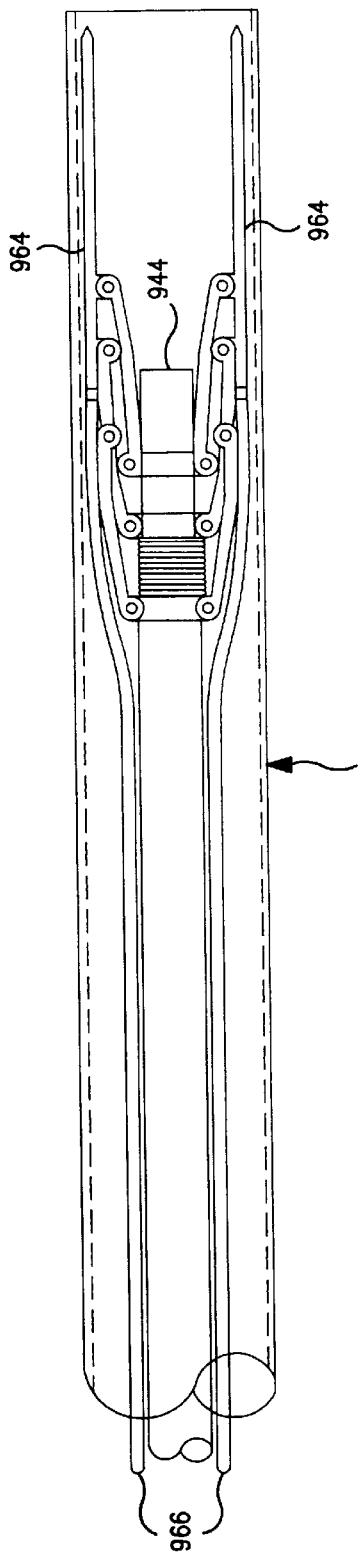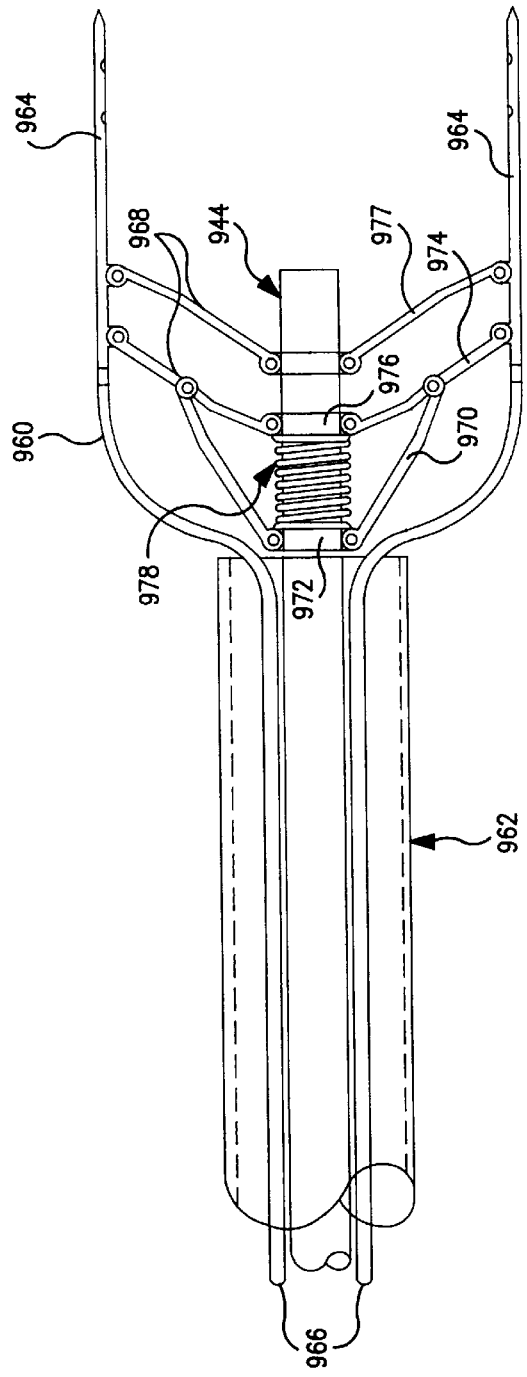
FIG. 9A
FIG. 9B

APPARATUS FOR ADDRESSING NEEDLE ARRAY ELECTRODES FOR ELECTROPORATION THERAPY

BACKGROUND OF THE INVENTION

1. Field of the Invention

The present invention relates generally to the use of electric pulses to increase the permeability of cell, and more specifically to a method and apparatus for the application of controlled electric fields for in vivo delivery of pharmaceutical compounds and genes into cells by electroporation therapy (EPT), also known as cell poration therapy (CPT) and electrochemotherapy (ECT).

2. Description of the Related Art

In the 1970's it was discovered that electric fields could be used to create pores in cells without causing permanent damage. This discovery made possible the insertion of large molecules into cell cytoplasm. It is known that genes and other molecules such as pharmacological compounds can be incorporated into live cells through a process known as electroporation. The genes or other molecules are mixed with the live cells in a buffer medium and short pulses of high electric fields are applied. The cell membranes are transiently made porous and the genes or molecules enter the cells, where they can modify the genome of the cell.

Electroporation in vivo is generally limited to tissue or cells that are close to the skin of the organism where the electrodes can be placed. Therefore, tissue which would otherwise be treatable by systemic drug delivery or chemotherapy, such as a tumor, is generally inaccessible to electrodes used for electroporation. In the treatment of certain types of cancer with chemotherapy, it is necessary to use a high enough dose of a drug to kill the cancer cells without killing an unacceptable high number of normal cells. If the chemotherapy drug could be inserted directly inside the cancer cells, this objective could be achieved. Some of the anti-cancer drugs, for example, bleomycin, normally cannot penetrate the membranes of certain cancer cells effectively. However, electroporation makes it possible to insert bleomycin into cells.

Treatment typically is carried out by injecting an anticancer drug directly into the tumor and applying an electric field to the tumor between a pair of electrodes. The field strength must be adjusted reasonably accurately so that electroporation of the cells of the tumor occurs without damage, or at least minimal damage, to any normal or healthy cells. This can normally be easily carried out with external tumors by applying the electrodes to opposite sides of the tumor so that the electric field is between the electrodes. When the field is uniform, the distance between the electrodes can then be measured and a suitable voltage according to the formula E=V/d can then be applied to the electrodes (E=electric field strength in V/cm; V=voltage in volts; and d=distance in cm). When large or internal tumors are to be treated, it is not easy to properly locate electrodes and measure the distance between them. The aforementioned parent application discloses a system of electrodes for in vivo electroporation wherein the electrodes may be inserted into the tumor. In related U.S. Pat. No. 5,273,525, a syringe for injecting molecules and macromolecules for electroporation utilizes needles for injection which also function as electrodes. This construction enables subsurface placement of electrodes.

Treatment of a subject using cell poration therapy provides a means for avoiding the deleterious effects typically associated with administration of anticancer or cytotoxic agents. Such treatment would allow introduction of these agents to selectively damage or kill undesirable cells while avoiding surrounding healthy cells or tissue.

SUMMARY OF THE INVENTION

It is a primary object of the invention to provide an improved apparatus that can be conveniently and effectively positioned to generate predetermined electric fields in preselected tissue.

In accordance with a primary aspect of the invention, an electrode apparatus for the application of electroporation to a portion of the body of a patient comprises a support member, a plurality of needle electrodes mounted on said support member for insertion into tissue at selected positions and distances from one another, and means including a signal generator responsive to said distance signal for applying an electric signal to the electrodes proportionate to the distance between said electrodes for generating an electric field of a predetermined strength.

The invention includes needles that function for injection of therapeutic substances into tissue and function as electrodes for generating electric fields for portion of cells of the tissue.

One embodiment of the invention includes a system for clinical electroporation therapy that includes a needle array electrode having a "keying" element, such as a resistor or active circuit, that determines the set point of the therapy voltage pulse, as well as selectable array switching patterns (the apparatus having this system has been termed MedPulser™). A number of electrode applicator designs permit access to and treatment of a variety of tissue sites.

Another embodiment of the invention provides a laparoscopic needle applicator that is preferably combined with an endoscope for minimally invasive electroporation therapy.

The invention provides a therapeutic method utilizing the needle array apparatus for the treatment of cells, particularly tumor cells.

BRIEF DESCRIPTION OF THE DRAWINGS

FIGS. 2a–2g are diagrammatic illustrations of several alternative electrode embodiments in accordance with the invention.

FIGS. 9a–9b show in detail an extending/retracting needle array in accordance with the invention.

Like reference numbers and designations in the various drawings indicate like elements.

DETAILED DESCRIPTION OF THE PREFERRED EMBODIMENTS

Overview

The invention provides an apparatus and a method for the therapeutic application of electroporation. The method includes injection of a chemotherapeutic agent or molecule and electroporation of the agent or molecule into a tumor. In particular, an agent or molecule is injected into tissue and voltage pulses are applied between "needle" electrodes disposed in the tissue, thus applying electric fields to cells of the tissue. The needle electrode assemblies described below enable the in vitro or in vivo positioning of electrodes in or adjacent to subsurface tumors or other tissue. Such therapeutic treatment is called electroporation therapy (EPT), also called electrochemotherapy. While the focus of the description below is EPT, the invention may be applied to other treatments, such as gene therapy of certain organs of the body.

For a general discussion of EPT, see co-pending application Ser. No. 08/537,265, filed on Sep. 29, 1995, which is a continuation-in-part of application Ser. No. 08/467,566 filed on Jun. 6, 1995, which is a continuation-in-part of application Ser. No. 08/042,039 filed on Apr. 1, 1993 now abandoned, all of which are incorporated herein by reference.

Electrode Assemblies

Figure 1:
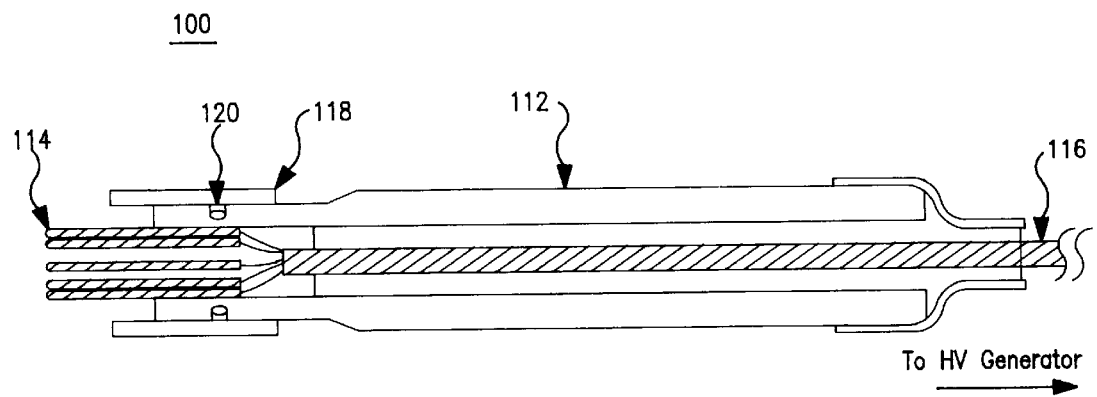
FIG. 1 is a cross-section assembly drawing showing a view of an embodiment of the invention.

FIG. 1 is a cross-section assembly drawing showing a view of a needle assembly 100 in accordance with one embodiment of the invention. The needle assembly 100 comprises an elongated tubular support body or shaft 112, which may be hollow stainless steel or a medical-grade plastic (e.g., nylon). If the shaft is made of a conductive material, electrical insulation should be applied on the exterior services to protect both patient and physician. The shaft 112 includes a plurality of electrode needles 114 at the distal end, coupled to respective conductors of a multi-conductor wire cable 116. The electrode needles 114 may be sharp or blunt, hollow or solid, and of any desired length. The material of the electrode needles 114 must be electrically conductive, but need not be a metal or uniform (i.e., a composite or layered structure may be used, such as metal-coated plastic or ceramic needles). One or more hollow electrode needles 114 may be used to inject a therapeutic substance. In different embodiments, the electrode needles 114 may comprise a rectangular, hexagonal, or circular array. However, other patterns may be used.

In use, the multi-conductor wire cable 116 is coupled to a high-voltage generator. In the illustrated embodiment, a retractable shield 118, restricted by a friction O-ring 120 near the distal end, can be slide fore and aft along the shaft 112 body to protect or expose the electrode needles 114.

FIGS. 2a–2e are diagrammatic illustrations of several alternative electrode embodiments in accordance with the invention. FIGS. 2a and 2b show straight-bodied electrodes having needles 200 with different spacing. For example, the needles in FIG. 2a comprise a 0.5 cm diameter array, while the needles in FIG. 2b comprise a 1.4 cm diameter array. The various body dimensions may vary as well. For example, the electrode in FIG. 2a has a stepped body structure, with a smaller diameter fore-body 202 relative to a larger diameter aft-body 204. The electrode in FIG. 2b has a uniform diameter body 206. The electrodes in FIGS. 2a and 2b are particularly well suited for treating small surface tumors.

FIGS. 2c and 2d show angled-head electrodes having needle tips 200 set at an angle with respect to the bodies 206 of the electrodes. FIG. 2c shows the needle-tips at about a 45° angle with respect the body 206. FIG. 2d shows the needle-tips at about a 90° angle with respect the body 206. The electrodes in FIGS. 2c and 2d are particularly well suited for treating head and neck tumors.

FIG. 2e shows a double-angled electrode having needle tips 200 set at an angle with respect to a smaller diameter fore-body 202. A larger diameter aft-body 204 is angled as well. The electrode in FIG. 2e is particularly well suited for treating tumors of the larynx, but may also be used in other body cavities.

Figure 2F:
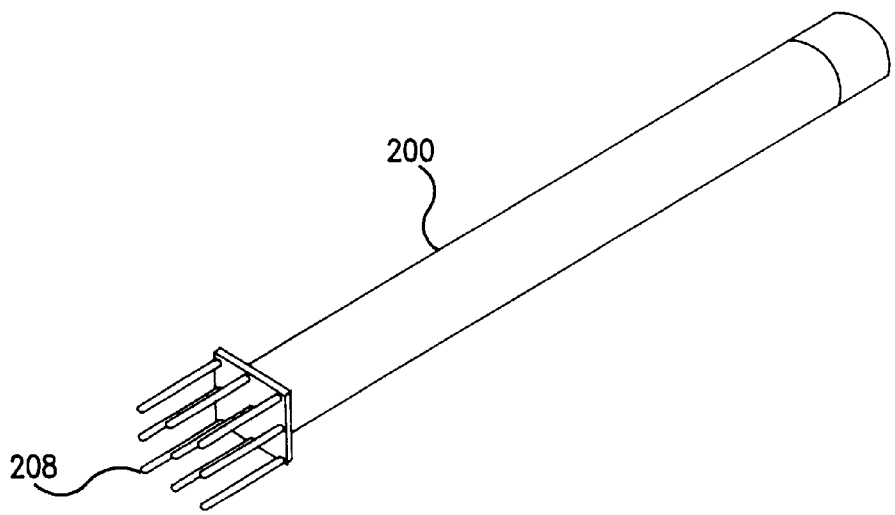
Figure 2G:
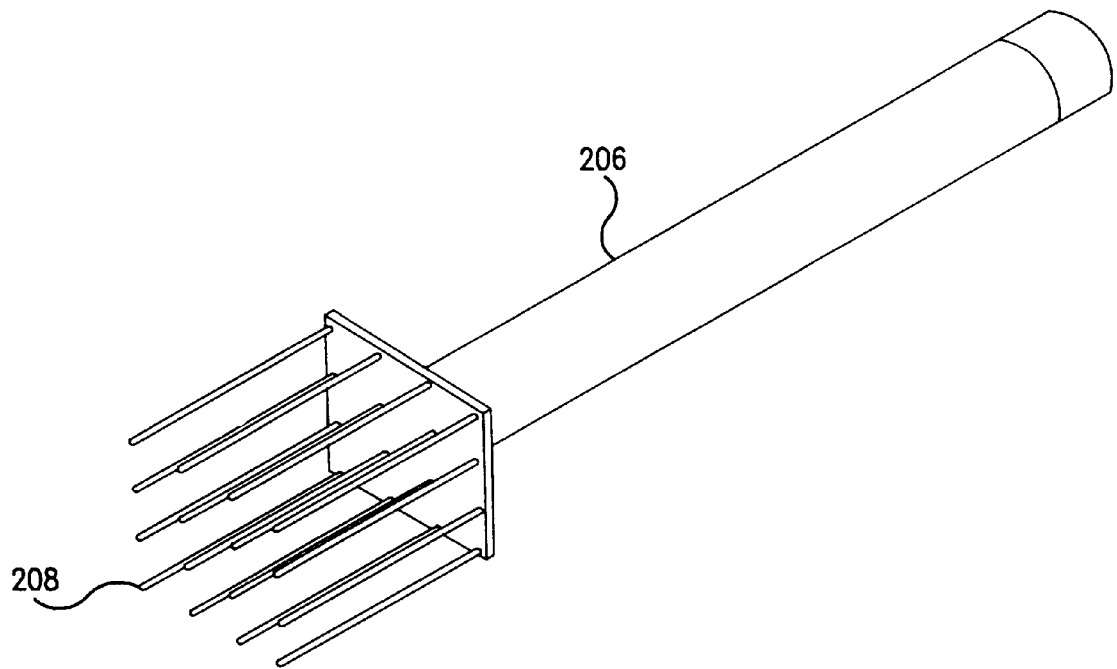

FIG. 2f shows an electrode particularly well suited for treating large tumors. The spacing between needles 208 may be, for example, about 0.65 cm. FIG. 2g shows an electrode particularly well suited for treating internal tumors. The spacing between needles 208 may be, for example, about 1.0 cm.

Any of the separate configuration elements (e.g., body size and configuration, head and body angle, etc.) shown in FIGS. 2a–2g can be combined as desired. Other configurations of electrode assemblies may be used to meet particular size and access needs.

EPT Instrument

Figure 3:
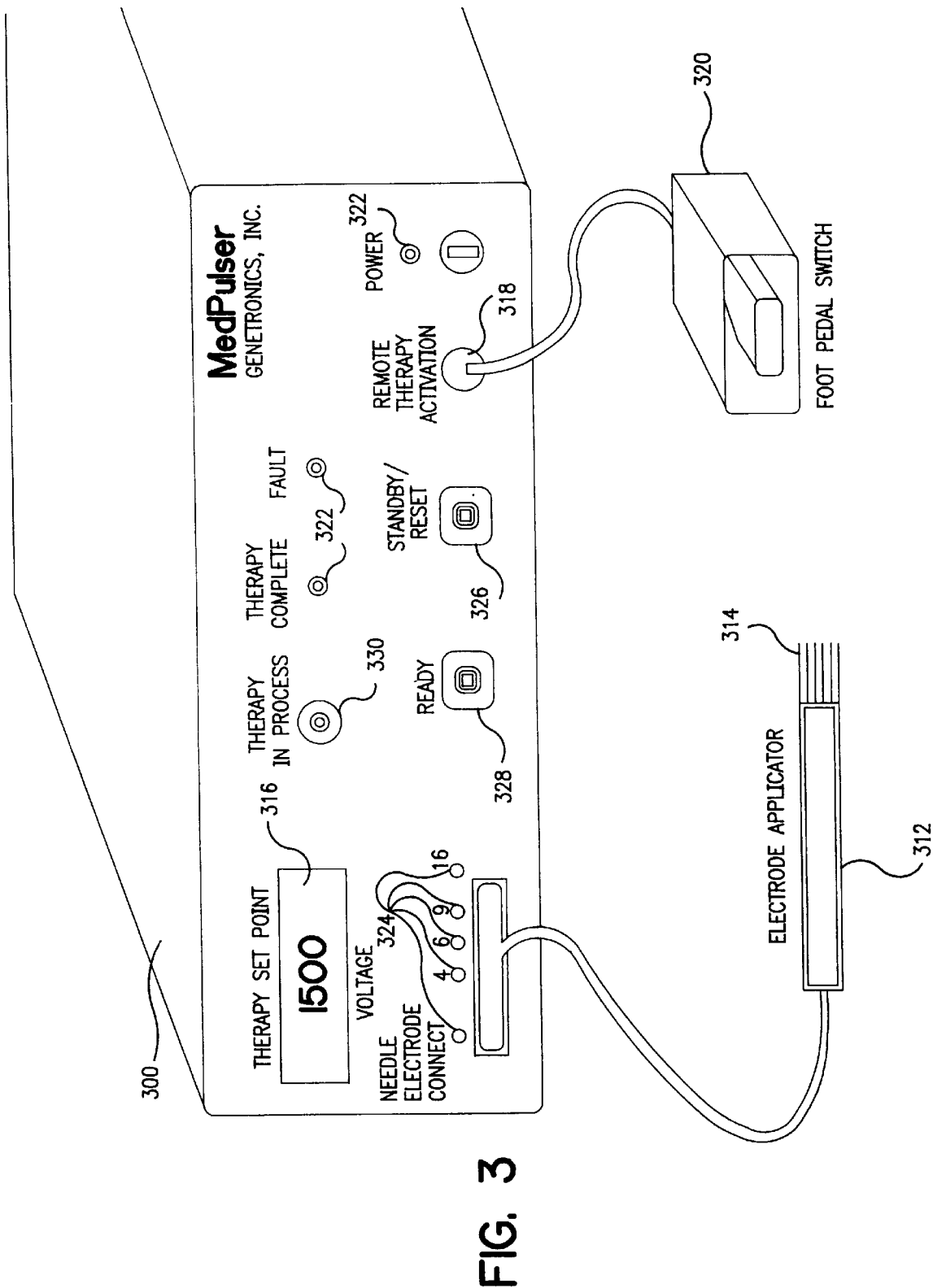
FIG. 3 is a block diagram of a treatment instrument in accordance with the invention.

FIG. 3 is a diagram of an EPT treatment instrument 300 embodying the invention. An electrode applicator 312 is removably coupled to the instrument 300, which selectively applies voltage pulses to selected electrode needles 314 of the electrode applicator 312. The pulse duration, voltage level, and electrode needle addressing or switching pattern output by the instrument 300 are all programmable.

A display 316 indicates the therapy voltage setpoint. A remote therapy activation connection 318 is provided to a accommodate a foot pedal switch 320 for activating pulses to the electrode applicator 312. The foot pedal switch 320 permits a physician to activate the instrument 300 while freeing both hands for positioning of the electrode applicator 312 in a patient's tissue. Indicator lights 322 for fault detection, power on, and completion of a therapy session are provided for convenience. Other indicator lights 324 are provided to positively indicate that an electrode applicator 312 is connected to the instrument 300 and to indicate the type of needle array (see discussion below). A standby/reset button 326 is provided to "pause" the instrument and reset all functions of the instrument to a default state. A ready button 328 is provided to prepare the instrument 300 for a therapy session. A prominent "therapy in process" indicator light 330 indicates that voltage pulses are being applied to the electrode needles 314. In addition, the instrument 300 may have audio indicators for such functions as a button press, a fault state, commencement or termination of a therapy session, indication of therapy in process, etc.

In an alternative embodiment, the instrument 300 can be coupled to a feedback sensor that detects heart beats. Applying pulses near the heart may interfere with normal heart rhythms. By synchronizing application of pulses to safe periods between beats, the possibility of such interference is reduced.

Figure 4A:
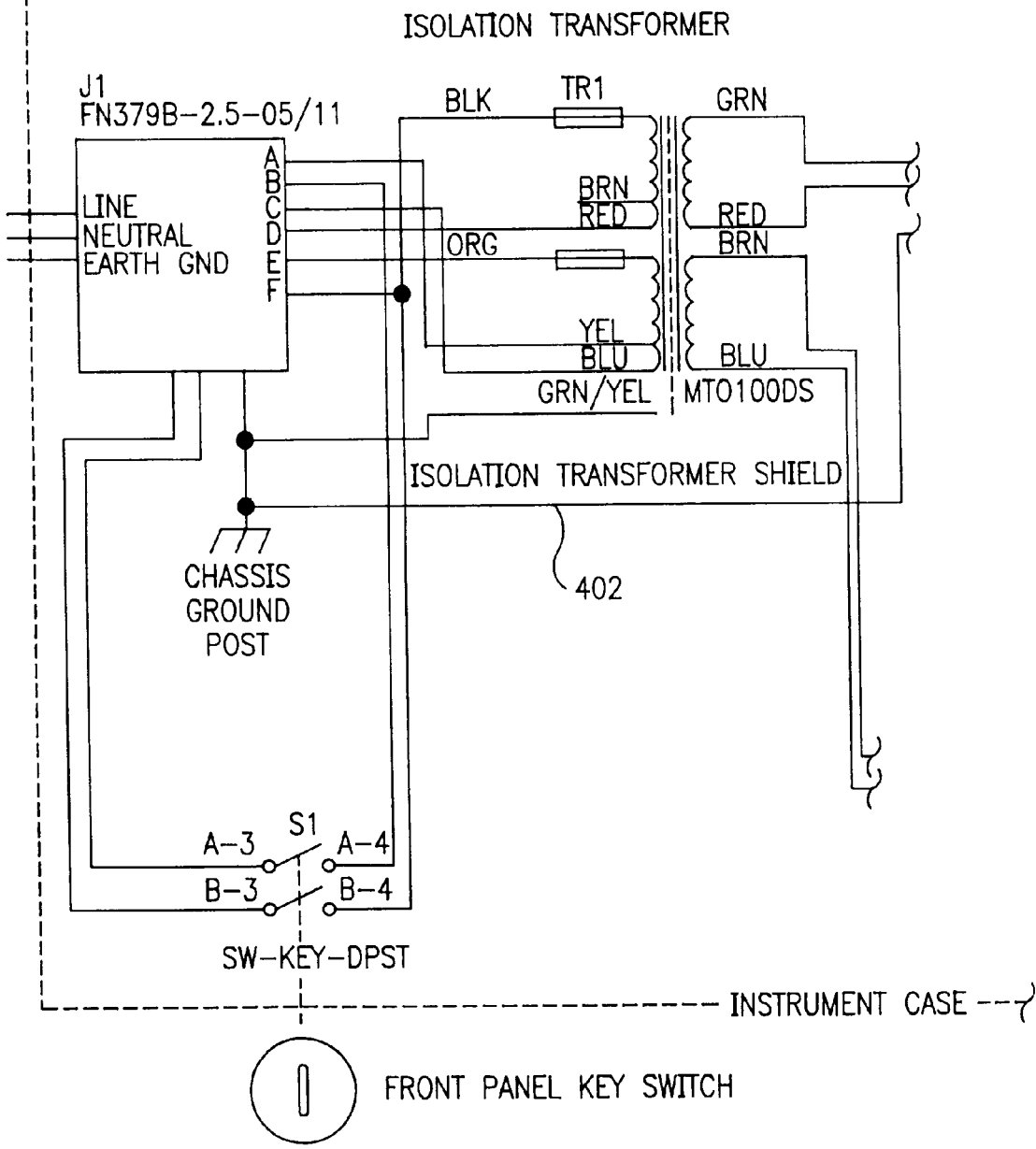
FIGS. 4A–C are a schematic block diagram of the circuitry for the treatment instrument of FIG. 3.
Figure 4B:
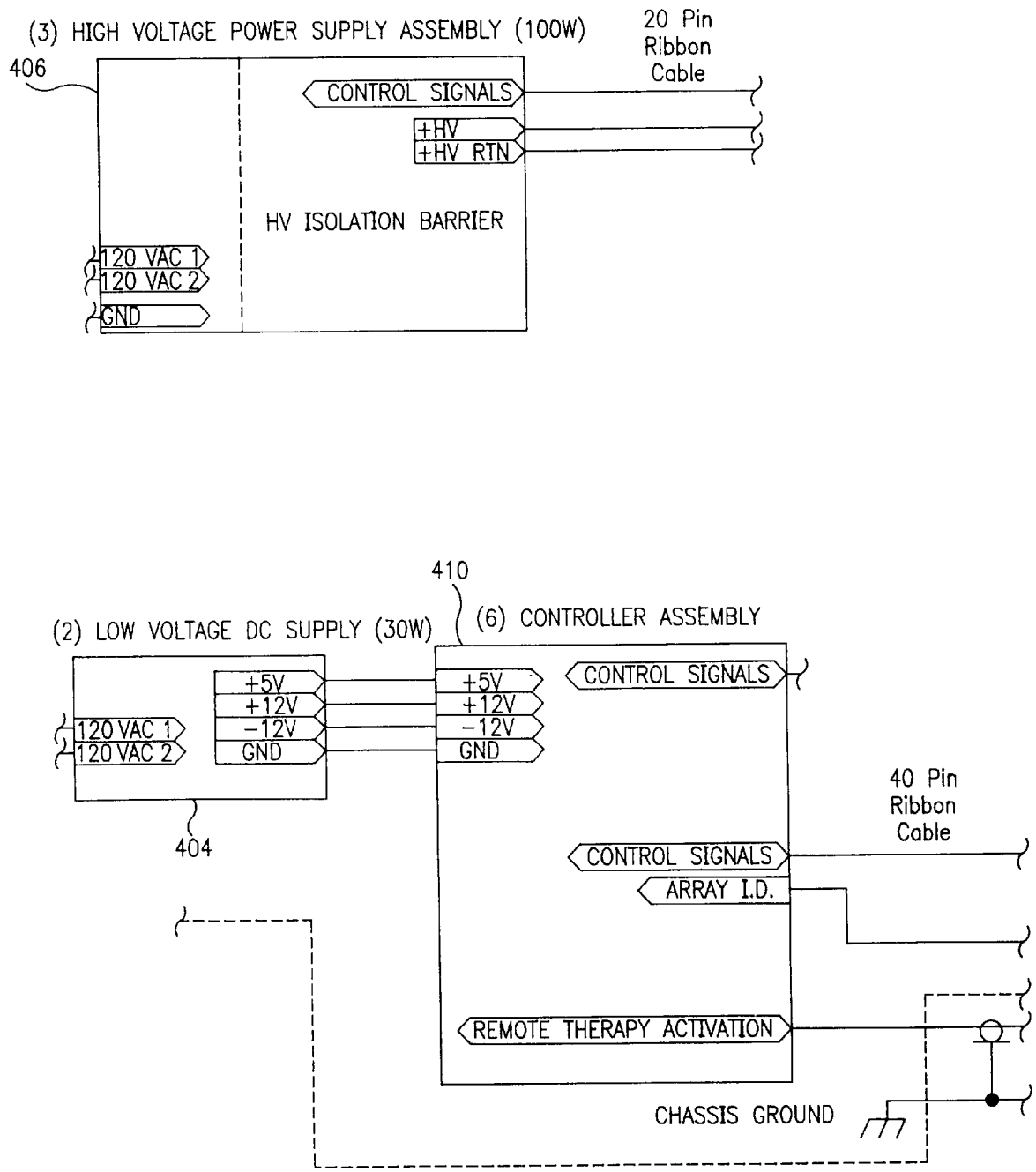
Figure 4C:
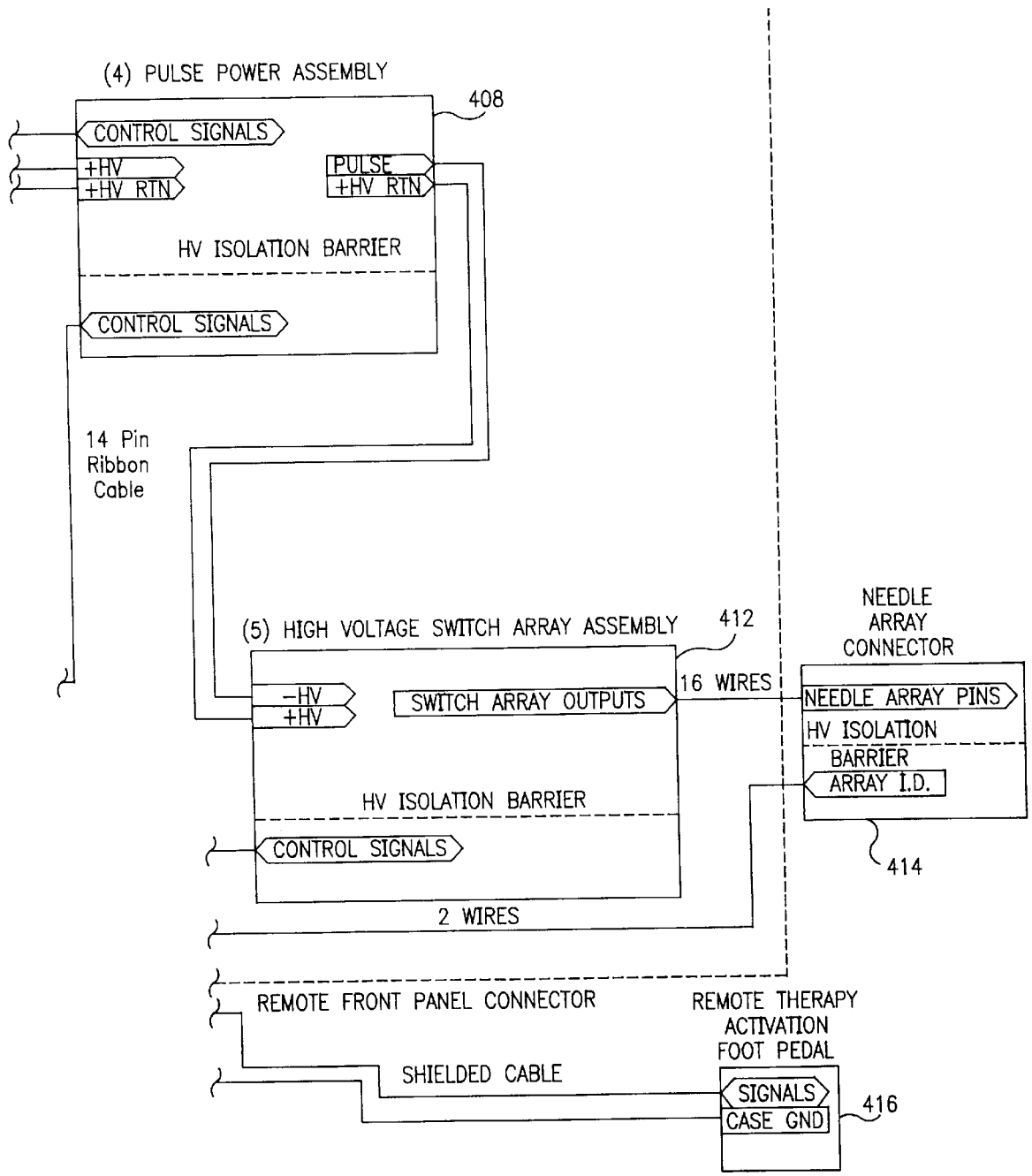

FIG. 4 is a schematic block diagram of the circuitry 400 for the treatment instrument 300 of FIG. 3. An AC power input module 402 provides electrically isolate power for the entire instrument 300. A low-voltage DC power supply 404 provides suitable power for the control circuitry of the instrument 300. A high-voltage power supply 406 provides suitable high voltages (e.g., up to several thousand volts) needed for EPT therapy. The output of the high-voltage power supply 406 is coupled to a pulse power assembly 408 which generates pulses of variable width and voltage under control from a controller assembly 410. The output of the pulse power assembly 408 is coupled through a high voltage switch array 412 to a needle array connector 414. A remote therapy activation foot peddle connector 416 permits attachment of a foot pedal switch 320.

The high voltage switch array 412 allows the necessary high voltages for EPT to be applied to selected subgroups of electrodes in a needle assembly 100. In prior versions of EPT instruments, application of such voltages has typically involved use of a manual rotary "distributor" switch, or a motorized version of such a switch. However, in the present invention, all switching is by electronically controlled relays, providing for faster and quieter switching, longer life, and better and more flexible control over switching patterns.

Figure 5:
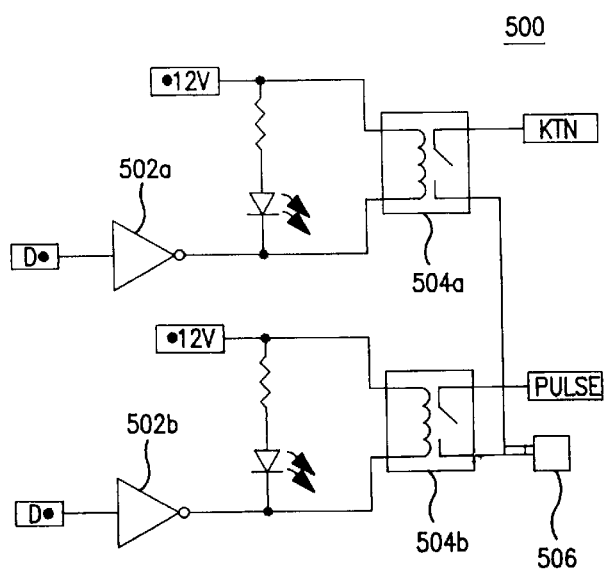
FIG. 5 is a schematic diagram of selector switching elements of the circuit shown in FIG. 4.

FIG. 5 is a schematic diagram of one selector switching element 500 of the high voltage switch array 412 of the circuit shown in FIG. 4. The number of such switching elements 500 should at least match the largest number of electrodes of any attached needle assembly 100. Each switching element 500 provides for control of the high-voltages applied to an electrode of a needle assembly 100, with the ability to provide voltage at either polarity to the associated electrode.

In particular, when a "negative" control voltage is applied to one inverting input amplifier 502a, an associated, normally open relay 504a is closed, establishing a negative return path for a pulse applied to a paired electrode to be coupled through an electrode connector 506. Similarly, when a "positive" control voltage is applied to a second inverting input amplifier 502b, an associated, normally open relay 504b is closed, establishing a path for a positive pulse to be applied to an electrode coupled through the electrode connector 506.

Needle Array Addressing

The instrument 300 of FIG. 3 is designed to accommodate electrode applicators 312 having varying numbers of electrode needles 314. Accordingly, an addressing scheme has been developed that, in the preferred embodiment, permits addressing up to 16 different needles, designated A through P, forming up to 9 square treatment zones and several types of enlarged treatment zones. A treatment zone comprises at least 4 needles in a configuration of opposing pairs that are addressed during a particular pulse. During a particular pulse, two of the needles of a treatment zone are of positive polarity and two are of negative polarity.

Figure 6:
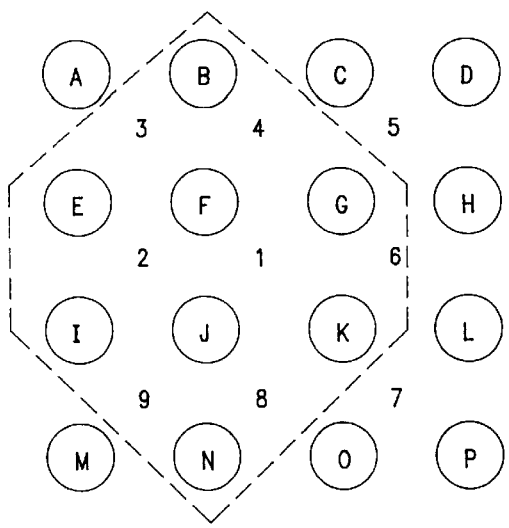
FIG. 6 diagrammatically shows a preferred 4×4 mapping array for needles forming 9 treatment zones in accordance with one embodiment of the invention.

FIG. 6 diagrammatically shows a preferred 4×4 mapping array for needles forming 9 square treatment zones numbered from the center and proceeding clockwise. In the preferred embodiment, this mapping, array defines 4-needle, 6-needle, 8-needle, 9-needle, and 16-needle electrode configurations. A 4-needle electrode comprises needles placed in positions F, G, K, and J (treatment zone 1). A 9-needle electrode comprises needles placed in positions defining treatment zones 1–4. A 16-needle electrode comprises needles placed in positions defining treatment zones 1–9.

Figure 7A:
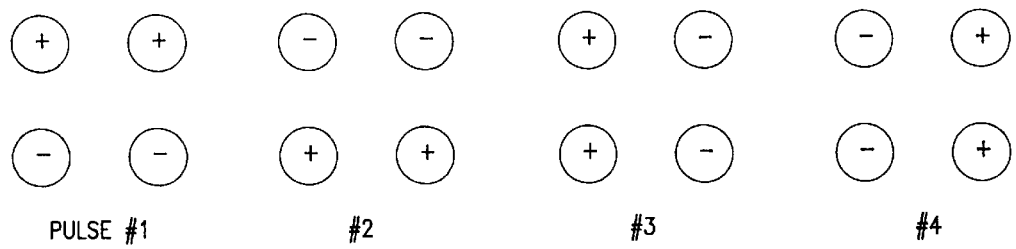
FIG. 7a shows a pulse sequence for a 2×2 treatment zone in accordance with one embodiment of the invention.

FIG. 7a shows a pulse sequence for a 2×2 treatment zone in accordance with one embodiment of the invention. During any of four pulses comprising a cycle, opposing pairs of needles are respectively positively and negatively charged, as shown. Other patterns of such pairs are possible, such as clockwise or counterclockwise progression. For a 9-needle electrode configuration, a preferred cycle comprises 16 pulses (4 treatment zones at 4 pulses each). For a 16-needle electrode configuration, a preferred cycle comprises 36 pulses (9 treatment zones at 4 pulses each).

Figures 7B, 7C, 7D:
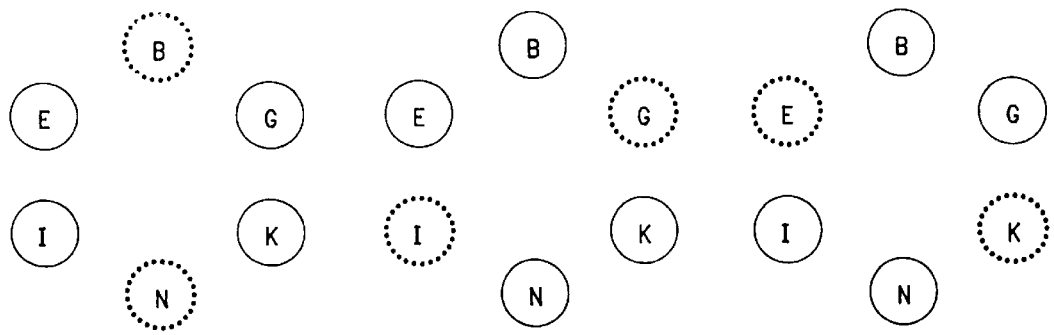
FIGS. 7b–7d shows a pulse sequence for a 6 needle array in accordance with one embodiment of the invention.

A 6-needle electrode configuration can comprise a circular or hexagonal array as shown in FIGS. 7b–7d. Alternatively, a 6-needle electrode configuration can be defined as a subset of a larger array, such as is shown in FIG. 6. For example, with reference to FIG. 6, a 6-needle electrode configuration can be defined as a 2×3 rectangular array of needles placed in positions defining treatment zones 1–2 (or any other linear pair of treatment zones), or a hexagonal arrangement of needles B, G, K, N, I, E (or any other set of positions defining a hexagon) defining an enlarged treatment zone (shown in dotted outline in FIG. 6). Similarly, an 8-needle electrode can comprise an octagon, or a subset of the larger array shown in FIG. 6. For example, with reference to FIG. 6, an 8-needle electrode can be defined as a 2×4 array of needles placed in positions defining treatment zones 1, 2 and 6 (or any other linear triplet of treatment zones), or an octagonal arrangement of needles B, C, H, L, O, N, I, E (or any other set of positions defining an octagon) defining an enlarged treatment zone.

FIGS. 7b–7d shows a hexagonal arrangement and one possible activation sequence. FIG. 6b shows a first sequence, in which needles G and K are positive and needles I and E are negative during a first pulse, and have reversed polarities during a next pulse; needles B and N, shown in dotted outline, are inactive. FIG. 6c shows a second sequence, in which needles K and N are positive and needles E and B are negative during a first pulse, and have reversed polarities during a next pulse; needles G and I are inactive. FIG. 6de shows a third sequence, in which needles N and I are positive and needles B and G are negative during a first pulse, and have reversed polarities during a next pulse; needles K and E are inactive. A total of 6 pulses are applied in a cycle of sequences. A similar activation sequence can be used for an octagonal arrangement.

Regardless of physical configuration, the preferred embodiments of the invention always uses at least two switched pairs of electrodes (for example, as shown in FIG. 7a) in order to achieve a relatively uniform electric field in tissue undergoing EPT. The electric field intensity should be of sufficient intensity to allow incorporation of a treatment agent in order to effect the process of electroporation.

Automatic Identification of Electrode Applicators

The mapping scheme described above permits different electrode applicators 312 to be coupled to the same instrument 300. Since the number of electrode needles 314 can vary, the invention includes a means for automatically configuring the instrument 300 to address the proper number of electrode needles 314. In one embodiment, each electrode applicator 312 includes a built-in type identification element, such as a "keying" resistor, that permits the instrument 300 to determine the number of electrode needles 314, and thus set itself to a matching addressing scheme. The instrument 300 reads the type identification element when an electrode applicator 312 is coupled to the instrument 300. The type identification element may be incorporated into a connector for the electrode applicator 312 and access through shared or dedicated electrical connections.

As an illustrative example, the following table maps resistor values to the number of electrode needles 314:

| Needle Array Type ID Resistor (ohms) | Needle Addressing Scheme |
|---|---|
| 787 | 6 |
| 453 | 6 |
| 232 | 6 |
| 4.32K | 9 |
| 2.21K | 16 |
| 1.29K | 16 |

A similar technique can be used to automatically set the therapy voltage for the instrument 300. That is, each electrode applicator 312 includes a built-in voltage identification element, such as a "keying" resistor, that permits the instrument 300 to determine the proper voltage level for treatment pulses for the particular electrode applicator 312. The instrument 300 reads the voltage identification element when an electrode applicator 312 is coupled to the instrument 300.

As an illustrative example, the following table maps resistor values to setpoint voltages:

| Needle Array Voltage ID Resistor (ohms) | Setpoint Voltage |
|---|---|
| 787 | 560 |
| 453 | 1130 |
| 232 | 1500 |
| 4.32K | 845 |
| 2.21K | 845 |
| 1.29K | 1300 |

The same or different identification elements may be used for type identification and voltage identification. The nature of the identification element may vary as well. For example, an electronic circuit may be incorporated into each electrode applicator 312 with stored digital or analog values for a variety of variables. Examples of information that may be coded into an electrode applicator 312 are: needle array type parameters, such as number of needles, needle spacing, needle array geometry, and/or needle switching sequence; electrical pulse parameters such as voltage setpoint, pulse length, and/or pulse shape; shelf life; and usage limit. If the electrode applicator 312 uses a writable active circuit which can store data (e.g., an NVRAM), other information which can be coded into an electrode applicator 312 include: shelf life lockout (i.e., a code that disables use of an electrode applicator 312 if its shelf life has expired); a usage count and lockout (i.e., a code that disables use of an electrode applicator 312 if the number of allowed uses has been reached; when an electrode applicator 312 is designed to be disposable, this feature prevents contamination from re-use); usage history (e.g., a log which records the number of pulses applied, date and time of application, etc.); and error code capture (e.g., to allow an electrode applicator 312 to be returned to the manufacturer and analyzed for failure modes of the applicator or of the instrument 300).

The lockout may be determined by the length of time from initial use of the applicator as well as the number of therapy applications from a single device. This may be accomplished by writing a time stamp to the disposable applicator "key" element active circuit upon initial connection to the instrument and would not allow use beyond a certain length of time afterward. The time length limitation would be determined by the maximum practical time length of one surgical procedure.

Furthermore, the usage of the "key" element may include manufacturing and quality control information. One example of such information is lot code of the device. Also, it may aid in the quality control of the device by not allowing untested material to be used, e.g., the device is configured for use only after it has successfully completed a manufacturing test inspection.

Laparoscopic Needle Applicator

Figure 8:
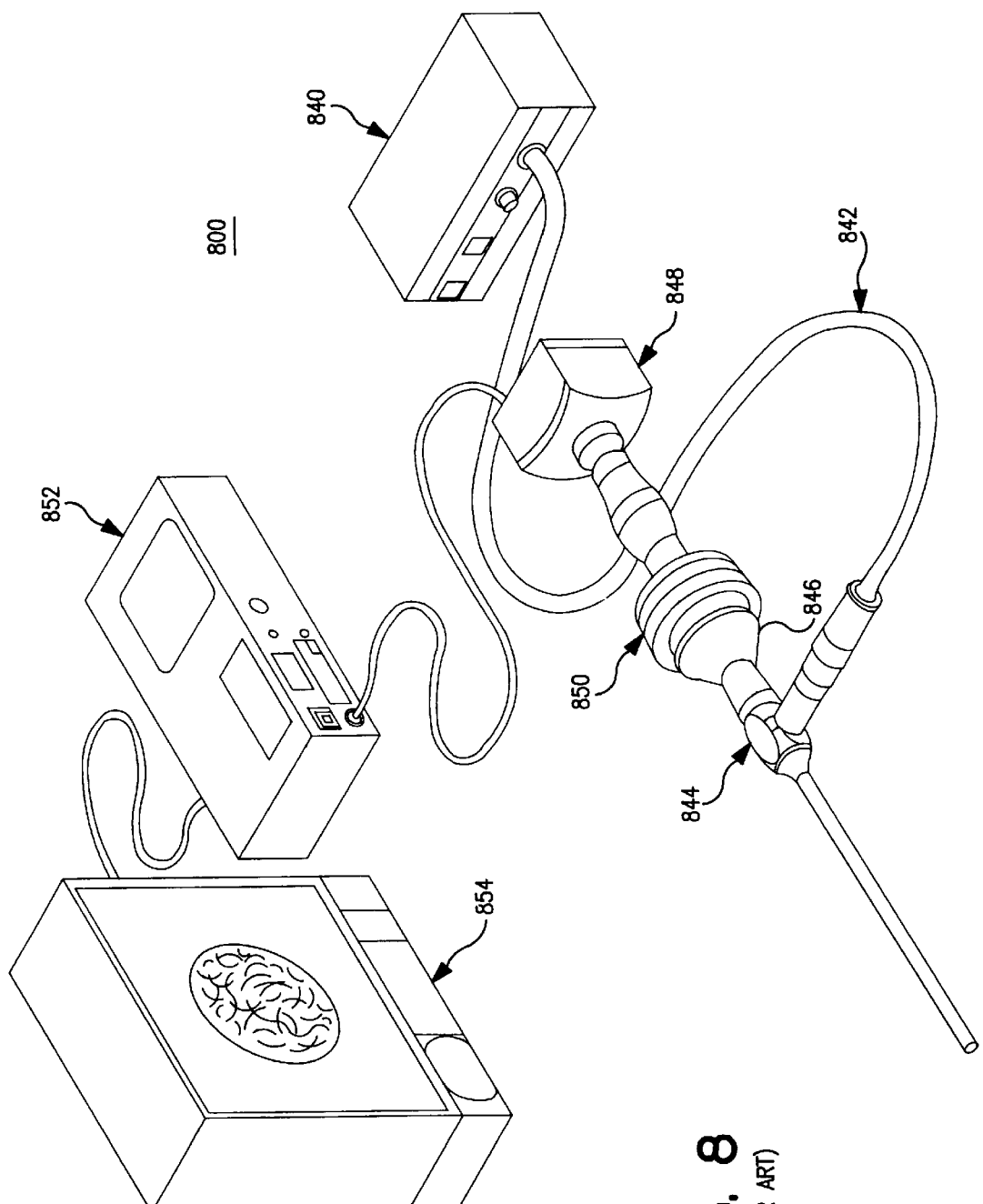
FIG. 8 is a diagram of a prior art endoscopic examination system.

One embodiment of the invention that is particular useful for treating internal tumors combines a laparoscopic needle array and the endoscopic examination system to permit minimally invasive EPT. FIG. 8 is a diagram of a prior art endoscopic examination system 800. Light from a light source 840 is transmitted through a fiber optic light guide 842 to an endoscope 844, in known fashion. Tissue is illuminated from light emanating from the distal end of the endoscope 844. Reflected light is gathered by the distal end of the endoscope 844 and transmitted to an eyepiece 846 or to a video camera 848 via an optical coupler 850. A signal from the video camera 848 may be recorded on a video cassette recorder 852 and/or displayed on a video monitor 854.

FIGS. 9a–9b are partially phantom side views of the distal end of an improvement over the endoscope 844 of FIG. 8, showing in detail an extending/retracting needle array 960 in accordance with the invention. A movable sheath 962 encloses an endoscope 944 and the needle array 960. FIG. 9a shows the sheath 262 in an extended position, fully covering the endoscope 944 and the needle array 960. FIG. 9b shows the sheath 962 in a retracted position, exposing the distal ends of the endoscope 944 and the needle array 960. (While the preferred embodiment uses a movable sheath 962, all that is required is relative movement between the sheath 962 and the endoscope 944; hence, the endoscope 944 may be regarded as the movable element.)

In the preferred embodiment, the needle array 960 includes at least two electrode needles 964, each coupled to a voltage supply (not shown), and at least one of which may be hollow and coupled via tubing 966 to a drug supply (not shown). The tips of the electrode needles 964 are preferably positioned to extend beyond the distal end of the endoscope 944, so that a tissue site can be viewed with the endoscope 944 while the electrode needles 964 are inserted into the tissue.

Each electrode needle 964 is coupled to a compressible mechanism 968. In the illustrated embodiment, the compressible mechanism 968 includes, for each electrode needle 964, a support arm 970 pivotably coupled to a slidable base 972 that is free to move along the endoscope 944, and to a primary extension arm 974. Each primary extension arm 974 is pivotably coupled to a fixed base 976 that is attached to the endoscope 944, and to a corresponding electrode needle 964. A secondary extension arm 977, similar in construction to the primary extension arm 974 (but without a support arm 970) is provided for added stability of the electrode needles 964 when in a deployed configuration, described below.

When the sheath 962 is in an extended position, the electrode needles 964 are in relatively close proximity to each other. While in some uses this degree of proximity may be adequate for particular voltages, in other uses the electrode needles 964 need to have greater separation.

Accordingly, in the preferred embodiment, when the sheath 962 is moved to the retracted position, a compression element 978 (e.g., a spring) biases each slidable base 972 away from the fixed base 976, causing each support arm 970 to pull on the coupled primary extension arm 974. This retractive force causes the extension arms 974, 977 to angle out from the endoscope 944 into a deployed configuration, thus increasing the separation between the electrode needles 964 as shown in FIG. 9b.

When the sheath 962 is moved to the extended position, the sheath 962 compresses the electrode needles 964 together, forcing the extension arms 974, 977 to fold. This causes each primary extension arm 974 to pull on the coupled support arm 970. The retractive force on each support arm 970 causes each slidable base 972 to move towards the fixed base 976 into a sheathed configuration, compressing the compression element 978, as shown in FIG. 9a.

Other compressible mechanisms 968 may be used to separate the electrode needles 964, as such as wedges (or a hollow core cone) of compressible elastomeric material (such as foam or rubber) lodged between the endoscope 944 and the electrode needles 964, such that the widest portion of the wedges are at the distal end of the endoscope 944. When the sheath 962 is in an retracted position, the elastomeric material expands more at the distal end of the wedges than at the proximal end of the wedges, thus increasing the separation between the electrode needles 964. Further, not every electrode needle 964 need be movable by a compressible mechanism 968. For example, sufficient separation between two electrode needles 964 may be achieved if one of the electrode needles 964 is held in a fixed position relative to the endoscope 944 while the other electrode needle 964 is movable between a compressed and extended position; the two electrode needles 964 would be asymmetrically disposed with respect to the endoscope 944 when in a deployed configuration.

In any case, the compressible mechanism 968 must provide electrical isolation between each electrode needle 964, and thus is preferably made in whole or in part of a dielectric such as non-conductive plastic.

While the preferred embodiment of a laparoscopic needle array includes an endoscope, in some embodiments it may be useful to use the laparoscopic needle array with a separate endoscope. In this configuration, a support rod can be substituted in FIGS. 15a and 15b for the endoscope 944.

Electric Field Parameters

The nature of the electric field to be generated is determined by the nature of the tissue, the size of the selected tissue and its location. It is desirable that the field be as homogenous as possible and of the correct amplitude. Excessive field strength results in lysing of cells, whereas a low field strength results in reduced efficacy. The electrodes may be mounted and manipulated in many ways including but not limited to those in the parent application. The electrodes may be conveniently manipulated on and by forceps to internal position.

The waveform of the electrical signal provided by the pulse generator can be an exponentially decaying pulse, a square pulse, a unipolar oscillating pulse train, a bipolar oscillating pulse train, or a combination of any of these forms. The nominal electric field strength can be from about 10 V/cm to about 20 kV/cm (the nominal electric field strength is determined by computing the voltage between electrode needles divided by the distance between the needles). The pulse length can be about 10 $\mu$s to about 100 ms. There can be any desired number of pulses, typically one to 100 pulses per second. The wait between pulses sets can be any desired time, such as one second. The waveform, electric field strength and pulse duration may also depend upon the type of cells and the type of molecules that are to enter the cells via electroporation.

The various parameters including electric field strengths required for the electroporation of any known cell is generally available from the many research papers reporting on the subject, as well as from a database maintained by GENETRONICS, INC., San Diego, Calif., assignee of the subject application. The electric fields needed for in vivo cell electroporation, such as EPT, are generally similar in magnitude to the fields required for cells in vitro. Recent investigation by the inventors show that the preferred magnitudes are in the range of from 10 V/cm to about 1300 V/cm. The higher end of this range, over about 600 V/cm, has been verified by in vivo experiments of others reported in scientific publications.

The nominal electric field can be designated either "high" or "low". Preferably, when high fields are used, the nominal electric field is from about 700 V/cm to 1300 V/cm and preferably from about 1000 V/cm to 1300 V/cm. Preferably, when low fields are used, the nominal electric field is from about 10 V/cm to 100 V/cm, and more preferably from about 25 V/cm to 75 V/cm. In a particular embodiment, it is preferred that when the electric field is low, the pulse length is long. For example, when the nominal electric field is about 25–75 V/cm, it is preferred that the pulse length is about 10 msec.

Preferably, the therapeutic method of the invention utilizes the apparatus of the invention which provides an electrode apparatus for the application of electroporation to a portion of the body of a patient comprises a support member, a plurality of needle electrodes mounted on said support member for insertion into tissue at selected positions and distances from one another, and means including a signal generator responsive to said distance signal for applying an electric signal to the electrodes proportionate to the distance between said electrodes for generating an electric field of a predetermined strength.

Alternatively, it is understood that other systems could be utilized in the therapeutic method of the invention (e.g., for low voltage, long pulse treatment), for example, a square wave pulse electroporation system. For example, the ElectroSquarePorator (T820), available from GENETRONICS, INC. of San Diego, Calif., U.S.A., can be used. Square wave electroporation systems deliver controlled electric pulses that rise quickly to a set voltage, stay at that level for a set length of time (pulse length), and then quickly drop to zero. This type of system yields better transformation efficiency for the electroporation of plant protoplast and mammalian cell lines than an exponential decay system.

The ElectroSquarePorator (T820) is the first commercially available square wave electroporation system capable of generating up to 3000 Volts. The pulse length can be adjusted from 5 μsec to 99 msec. The square wave electroporation pulses have a gentler effect on the cells which results in higher cell viability.

The T820 ElectroSquarePorator is active in both the High Voltage Mode (HVM) (100–3000 Volts) and the Low Voltage Mode (LVM) (10–500 Volts). The pulse length for LVM is about 0.3 to 99 msec and for HVM, 5 to 99 μsec. The T820 has multiple pulsing capability from about 1 to 99 pulses.

Therapeutic method

The therapeutic method of the invention includes electrotherapy, also referred to herein as electroporation therapy (EPT), using the apparatus of the invention for the delivery of macromolecules to a cell or tissue. As described earlier, the term "macromolecule" or "molecule" as used herein refers to drugs (e.g., chemotherapeutic agents), nucleic acids (e.g., polynucleotides), peptides and polypeptides, including antibodies. The term polynucleotides include DNA, cDNA and RNA sequences.

Drugs contemplated for use in the method of the invention are typically chemotherapeutic agents having an antitumor or cytotoxic effect. Such drugs or agents include bleomycin, neocarcinostatin, suramin, doxorubicin, carboplatin, taxol, mitomycin C and cisplatin. Other chemotherapeutic agents will be known to those of skill in the art (see for example The Merck Index). In addition, agents that are "membrane-acting" agents are also included in the method of the invention. These agents may also be agents as listed above, or alternatively, agents which act primarily by damaging the cell membrane. Examples of membrane-acting agents include N-alkylmelamide and para-chloro mercury benzoate. The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. In addition, certain agents may require modification in order to allow more efficient entry into the cell. For example, an agent such as taxol can be modified to increase solubility in water which would allow more efficient entry into the cell.

Electroporation facilitates entry of bleomycin or other similar drugs into the tumor cell by creating pores in the cell membrane.

In one embodiment, the invention provides a method for the therapeutic application of electroporation to a tissue of a subject for introducing molecules into cells therein, comprising providing an array of electrodes, at least one of the electrodes having a needle configuration for penetrating tissue; inserting the needle electrode into selected tissue for introducing molecules into the tissue; positioning a second electrode of the array of electrodes in conductive relation to the selected tissue; applying pulses of high amplitude electric signals to the electrodes, proportionate to the distance between the electrodes, for electroporation of the tissue. It should be understood that the electroporation of tissue can be performed in vitro, in vivo, or ex vivo. Electroporation can also be performed utilizing single cells, e.g., single cell suspensions or in vitro or ex vivo in cell culture.

It may be desirable to modulate the expression of a gene in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The invention also provides gene therapy for the treatment of cell proliferative or immunologic disorders mediated by a particular gene or absence thereof. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA for example.

Various viral vectors which can be utilized for gene therapy as taught herein include adenovirus, herpes virus, vaccinia, or, preferably, an RNA virus such as a retrovirus.

Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. The term "biological response modifiers" is meant to encompass substances which are involved in modifying the immune response. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and alpha-interferon, beta-interferon, and gamma-interferon and their subtypes.

Also included are polynucleotides which encode metabolic enzymes and proteins, including antiangiogenesis compounds, e.g., Factor VIII or Factor IX. The macromolecule of the invention also includes antibody molecules. The term "antibody" as used herein is meant to include intact molecules as well as fragments thereof, such as Fab and F(ab')$_2$.

Administration of a drug, polynucleotide or polypeptide, in the method of the invention can be, for example, parenterally by injection, rapid infusion, nasopharyngeal absorption, dermal absorption, and orally. In the case of a tumor, for example, a chemotherapeutic or other agent can be administered locally, systemically or directly injected into the tumor. When a drug, for example, is administered directly into the tumor, it is advantageous to inject the drug in a "fanning" manner. The term "fanning" refers to administering the drug by changing the direction of the needle as the drug is being injected or by multiple injections in multiple directions like opening up of a hand fan, rather than as a bolus, in order to provide a greater distribution of drug throughout the tumor. As compared with a volume that is typically used in the art, it is desirable to increase the volume of the drug-containing solution, when the drug is administered (e.g., injected) intratumorally, in order to insure adequate distribution of the drug throughout the tumor. For example, in the EXAMPLES using mice herein, one of skill in the art typically injects 50 $\mu$l of drug-containing solution, however, the results are greatly improved by increasing the volume to 150 $\mu$l. In the human clinical studies, approximately 20 ml was injected to ensure adequate perfusion of the tumor. Preferably, the injection should be done very slowly all around the base and by fanning. Although the interstitial pressure is very high at the center of the tumor, it is also a region where very often the tumor is necrotic.

Preferably, the molecule is administered substantially contemporaneously with the electroporation treatment. The term "substantially contemporaneously" means that the molecule and the electroporation treatment are administered reasonably close together with respect to time. The administration of the molecule or therapeutic agent can at any interval, depending upon such factors, for example, as the nature of the tumor, the condition of the patient, the size and chemical characteristics of the molecule and half-life of the molecule.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Besides the inert diluents, such compositions can also include adjuvants, wetting agents, emulsifying and suspending agents. Further, vasoconstrictor agents can be used to keep the therapeutic agent localized prior to pulsing.

Any cell can be treated by the method of the invention. The illustrative examples provided herein demonstrate the use of the method of the invention for the treatment of tumor cells, e.g., pancreas, lung, head and neck, cutaneous and subcutaneous cancers. Other cell proliferative disorders are amenable to treatment by the electroporation method of the invention. The term "cell proliferative disorder" denotes malignant as well as non-malignant cell populations which often appear to differ from the surrounding tissue both morphologically and genotypically. Malignant cells (i.e., tumors or cancer) develop as a result of a multi-step process. The method of the invention is useful in treating malignancies or other disorders of the various organ systems, particularly, for example, cells in the pancreas, head and neck (e.g., larynx, nasopharynx, oropharynx, hypopharynx, lip, throat,) and lung, and also including cells of heart, kidney, muscle, breast, colon, prostate, thymus, testis, and ovary. Further, malignancies of the skin, such as basal cell carcinoma or melanoma can also be treated by the therapeutic method of the invention (see Example 2). Preferably the subject is human, however, it should be understood that the invention is also useful for veterinary uses in non-human animals or mammals.

In yet another embodiment, the invention provides method for the therapeutic application of electroporation to a tissue of a subject for damaging or killing cells therein. The method includes providing an array of electrodes; positioning a second electrode of the array of electrodes in conductive relation to the selected tissue; and applying pulses of high amplitude electric signals to the electrodes, proportionate to the distance between the electrodes, for electroporation of the tissue. The method preferably utilizes low voltage and a long pulse length which precludes the need for additional cytotoxic or chemotherapeutic agents. For example, preferably the nominal electric field is from about 25 V/cm to 75 V/cm and the pulse length is from about 5 $\mu$sec to 99 msec.

The following examples are intended to illustrate but not limit the invention. While they are typical of those that might be used, other procedures known to those skilled in the art may alternatively be used.

EXAMPLES

The following examples illustrate the use of EPT in cell lines, animals and humans. Example 1 illustrates EPT in poorly differentiated human pancreatic tumors (Panc-3) xenografted subcutaneously on the flank of nude mice. Example 2 shows the results of clinical trials in humans using EPT for treatment of basal cell carcinomas and melanomas. Example 3 shows results of clinical trials in humans using EPT for treatment of head and neck tumors. Example 4 provides in vitro data for EPT utilizing low voltage (electric field) and long pulse length. The parameters for EPT are described in the examples; for Example 1 and for the head and neck clinical trials, the nominal electric field was 1300 V/cm and 6 pulses for 99–100 $\mu$sec, spaced at 1 second intervals. The clinical trials (Example 2) used similar parameters, however the electric field was 1130 V/cm.

(Nominal electric field (V/cm) is applied voltage (V) across the needle pairs divided by the distance between the needle pairs (cm).) The Examples illustrate the use of EPT for effectively killing undesired cell populations (e.g., a tumor) in vitro and in vivo.

Example 1—EPT for Treatment of Tumors in vivo

The single treatment procedure involved injection of bleomycin (0.5 units in 0.15 ml saline) intratumorally, using fanning, as described herein followed by application of six square wave electrical pulses, ten minutes later, using needle array electrodes as described in the present application, arranged along the circumference of a circle 1 cm in diameter. Needle array of variable diameters (e.g., 0.5 cm, 0.75 cm and 1.5 cm can also be used to accommodate tumors of various sizes. Stoppers of various heights can be inserted at the center of the array to make the penetration depth of the needles into the tumor variable. A built-in mechanism allowed switching of electrodes for maximum coverage of the tumor by the pulsed field. The electrical parameters were: 780 V/cm center field strength and 6×99 $\mu$s pulses spaced at 1 sec interval.

Results showed severe necrosis and edema in nearly all the mice at the treatment site. While there was a substantial reduction in the tumor volume (after a slight initial increase due to edema) of the mice in the treated group (D+E+; D=Drug, E=Electrical field), those in the control group (D+E−) increased dramatically. Histological analysis of tumor samples showed necrotic tumor cell ghosts in D+E+ group compared to a mixture of viable and necrotic cells in D+E− group. Preliminary studies with human non-small cell lung cancer (NSCLC) tumors xenografted onto nude mice have also shown very encouraging results with EPT treatment with bleomycin.

The tumor cell line Panc-3, a poorly differentiated adenocarcinoma cell line of the pancreas, was supplied by AntiCancer, Inc., San Diego. For EPT experiments, tissue taken from the stock mice, where the tumor line was maintained, was thawed and cut into very small pieces about 1 mm each, and 8–10 pieces were surgically xenografted in a subcutaneous sac made in left flank of nude mice, and then closed with 6.0 surgical suture. After the average tumor size reached about 5 mm, mice with palpable tumors were divided randomly, 10 mice for control group (D+E−; D=Drug, E=Electric field) and 10 mice for EPT treatment, namely bleomycin injection followed by pulsing (D+E+) from a BTX Square Wave T820 Generator. The tumor dimensions were measured and the tumor volume calculated using the formula:

$$(\Pi/6) \times a \times b \times c$$

where a, b, and c a are, respectively, the length, width and thickness of the tumor. 0.5 units Bleomycin (Sigma Chemicals) was dissolved in 0.15 ml of 0.9% NaCl and was injected in each mice intratumorally by fanning for both the control (D+E−) and the treated (D+E+) groups. Ten minutes after the injection, each mouse in the D+E+ group was pulsed from a BTX T820 square wave electroporator with a set of needle array electrodes as described in the present invention. Electrical parameters used were as follows: field strength 1300 V/cm, 6 pulses of 99 $\mu$s each, at 1 sec interval.

The mice were monitored every day for mortality and any signs of a diseased state were noted. The tumor dimensions were measured at regular intervals and tumor growth regression/progression monitored.

Figure 10:
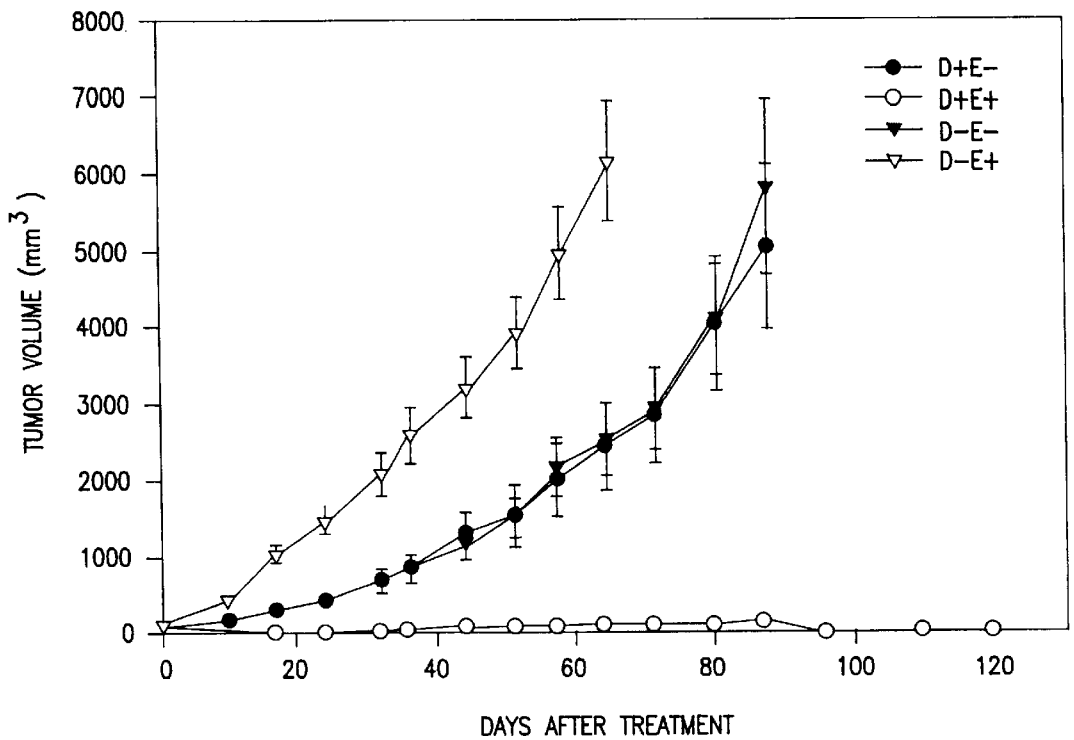
FIG. 10 shows the tumor volume up to 120 days of EPT with bleomycin in Panc-3 xenografted nude mice (D=drug; E=electroporation), for the venous control groups (D+E−, D−E−, D−E+), and the treated group (D+E+).
Figure 14A:
FIGS. 14a–14c show the histology of tumor samples carried out 35 days after the treatment. D+E+ group shows necrotic tumor cell ghosts (b) compared to a mixture of viable and nectrotic cells in D+E– group (a). Histology of samples from tumor site after 120 days show complete absence of tumor cells (c).
Figure 14B:
Figure 14C:
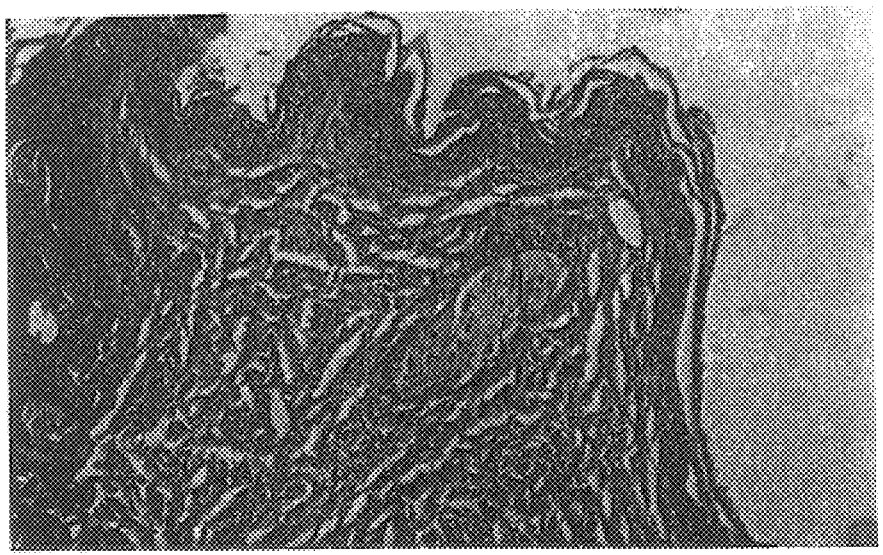

FIG. 10 shows the EPT results of various control and treated animals with and without drug and/or with and without pulsing using bleomycin for the Panc-3 tumors. There was a dramatic difference between the untreated and treated mice in terms of tumor volume. There was essentially no detectable tumor after approximately 24 days of treatment. The results of FIG. 10 are also summarized in Table 1 below up to 43 days. An illustration of the actual regression of the tumor is shown in the sequence of FIGS. 13a–13d and the corresponding histology in FIGS. 14a–14c.

TABLE 1

ELECTROCHEMOTHERAPY OF PANC-3 TUMORS IN NUDE MICE

| Days after treatment | Tumor volume ($mm^3$) C1 | Tumor volume ($mm^3$) C2 | Tumor volume ($mm^3$) T1 | Tumor volume ($mm^3$) T2 |
|---|---|---|---|---|
| 0 | 138.746 | 148.940 | 123.110 | 178.370 |
| 1 | 206.979 | 179.820 | 210.950 | 252.720 |
| 8 | 394.786 | 451.787 | 104.550 | 211.110 |
| 15 | 557.349 | 798.919 | 113.210 | 226.966 |
| 18 | 939.582 | 881.752 | 161.730 | 246.910 |
| 24 | 1391.057 | 1406.980 | 41.560 | 47.223 |
| 28 | 1628.631 | 1474.210 | 0 | 0 |
| 35 | 2619.765 | 2330.310 | 0 | 0 |
| 38 | 2908.912 | 2333.967 | 0 | 0 |
| 43 | 3708.571 | 5381.759 | 0 | 0 |

Cell Line: poorly differentiated human pancreatic tumor (Panc-3)
Mouse model: nude mouse
Transplant: subcutaneous xenograft
Control mice: C1 and C2
Treated mice: T1 and T2

Figure 12:
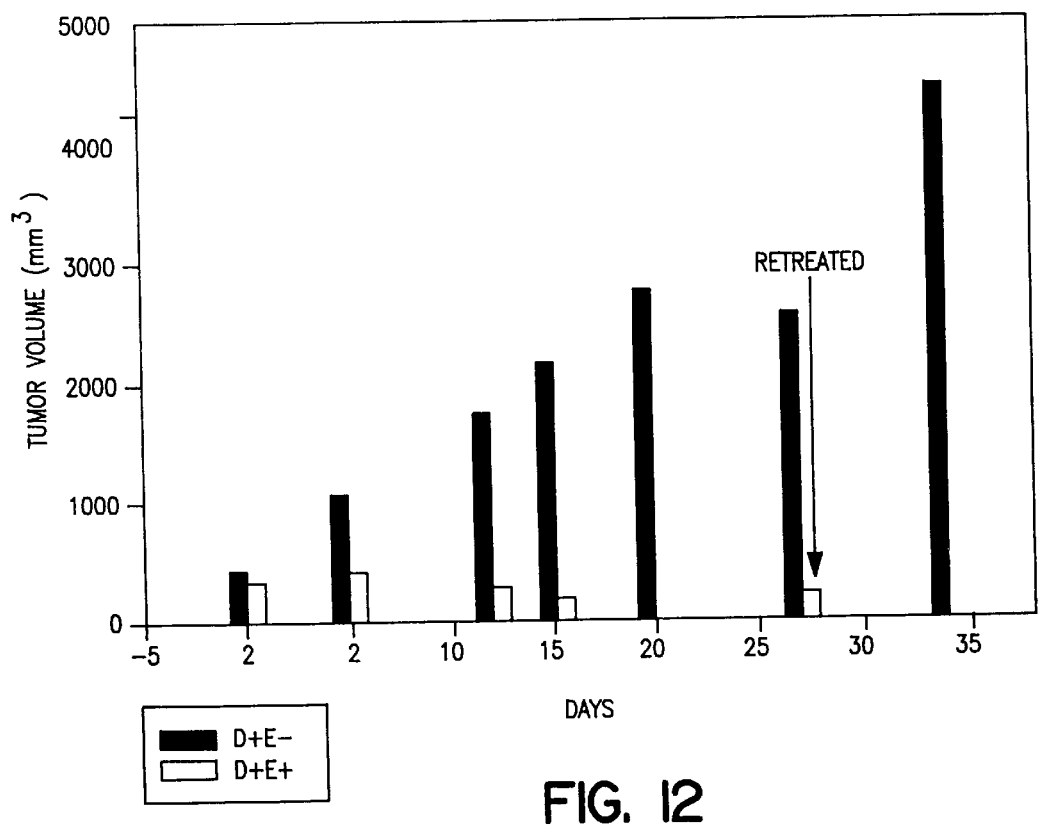
FIG. 12 shows the tumor volume after 34 days of EPT with bleomycin in non-small cell lung carcinoma (NSCLC) xenografted nude mice. The arrow indicates retreatment of one mouse at day 27 (D=drug; E=electroporation).
Figure 13A:
FIGS. 13a–13d show the sequences of events involved in the treatment of the tumor xenograft (a) by EPT. The treatment led to the formation of a scar (b) which dried and ultimately fell off (c) leaving a clear healed area of skin (d) free of tumor.
Figure 13B:
Figure 13C:
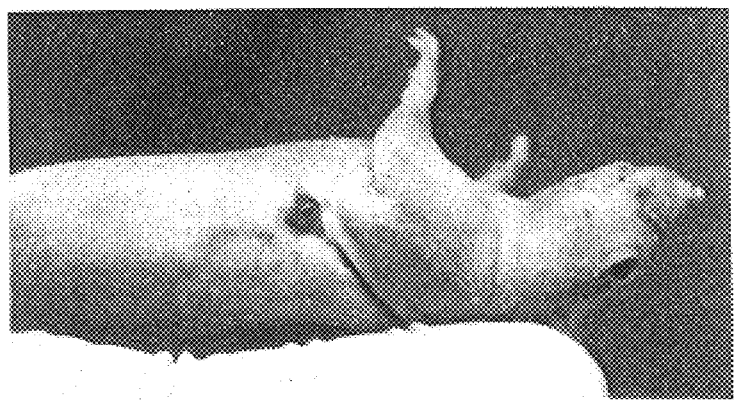
Figure 13D:

The Panc-3 experiment was repeated using a non-small cell lung cancer cell line (NSCLC), 177 (AntiCancer, San Diego, Calif.). The results were similar to that found with bleomycin and Panc-3 as shown in FIG. 10. In one experiment, a tumor that had recurred was retreated at day 27 (FIG. 12) and after 7 days, there was no evidence of tumor.

The Panc-3 and NSCLC models were utilized with the drug neocarcinostatin (NCS) following the same procedures as outlined above. As shown in FIG. 1 a, pre-pulse dosing with NCS in a manner similar to that used for the bleomycin studies, was not effective in reducing tumor size at all. It was believed that due to the low isoelectric point of NCS, electrostatic interaction prevented the drug from entering the tumor cell. Therefore, the experiment was repeated by pulsing first and injecting NCS post-pulse.

Figure 11A:
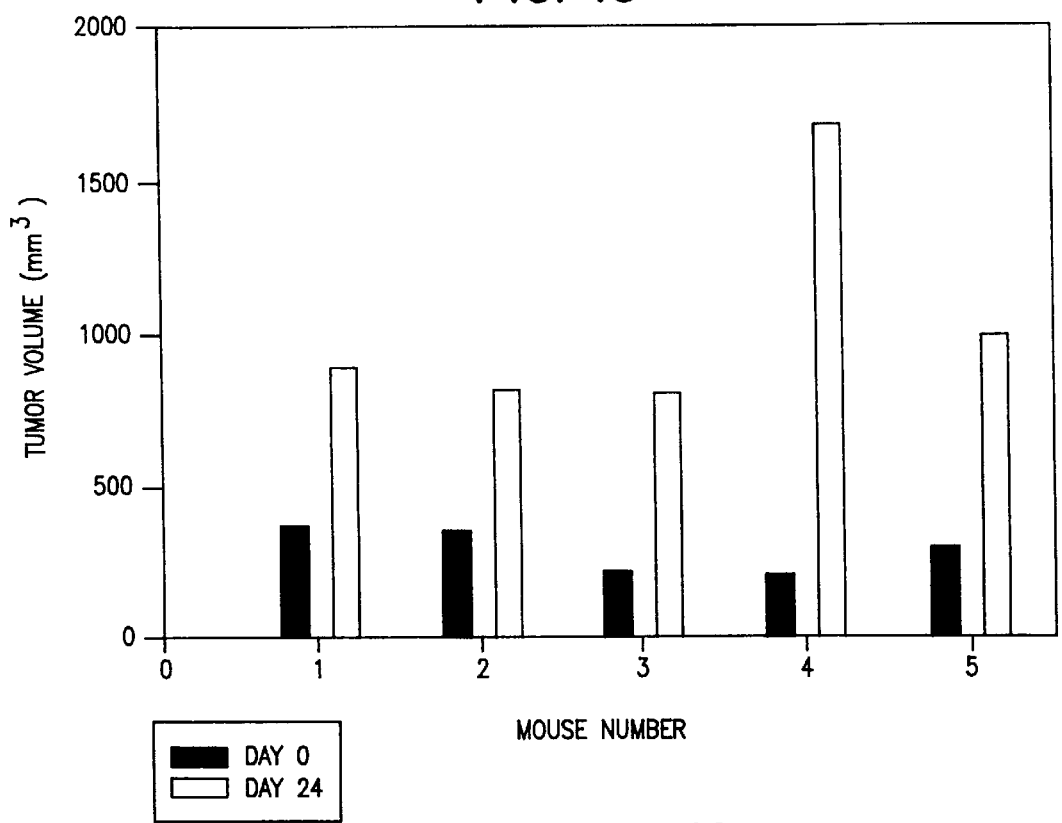
FIGS. 11a and 11b show the effect of EPT of Panc-3 with neocarcinostatin for the pre- and post-pulse injection of the drug, respectively, up to day 24.
Figure 11B:
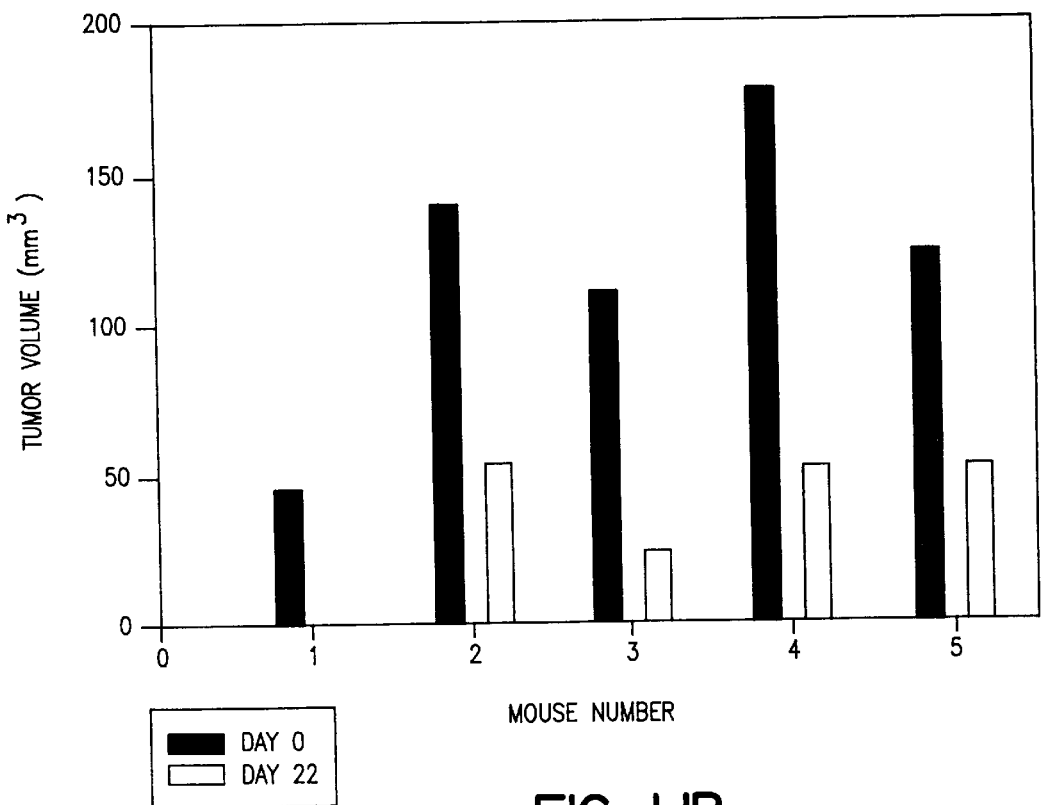

FIG. 11b shows the initial tumor volume (I) as compared to the final tumor volume (F) at day 13 for 7 mice treated (Mouse ID 1–7). In several of the mice (ID 1, 2, 4, and 7), an increase in tumor volume was observed, but appeared to be due to edema. However, as shown in FIG. 20d, when a separate group of 5 mice were examined at day 23, all mice showed a marked reduction in tumor volume.

A comparison of FIGS. 11a and 11b indicated that postpulse with NCS was more effective than pre-pulse administration for NCS.

The present Example illustrates that a poorly differentiated Pancreatic cancer (Panc-3) and Non-small cell lung cancer (NSCLC) xenografted subcutaneously onto nude mice can be effectively treated by the EPT method of the invention using bleomycin or NCS and needle array electrodes. Other similar chemotherapeutic agents can also be effective using the method of the invention.

The response of Panc-3 to ECT with bleomycin is shown in Table 2. In 68% (17/25) of the treated mice, complete tumor regression was observed 28 days following treatment, while 20% (5/25) showed partial (>80%) regression, 8% (2/25) showed no response and 4% (1/25) died, 20 days after treatment. No palpable tumor was observed in 64% (16/25) of the cases even after 120 days of the treatment. Representative animals (2/17) from this group were monitored to be without tumors for 243 days after which these were humanely euthanized. In 8% of the mice, however, there was tumor regrowth 35 days after treatment, but at a much slower rate.

Histological studies clearly showed severe necrosis of the tumor region for the group subjected to EPT whereas no necrosis was apparent in the control group. Intratumoral drug injection with larger volume of bleomycin, combined with fanning to maximize uniform drug distribution throughout the tumor volume, was found to be very effective as compared to the conventional mode of injecting the drug prior to pulsing.

TABLE 2

Electrochemotherapy of Panc-3 with Bleomycin

| Days after treatment Number of mice treated: 25 | 28 | 35 | 57 | 84 | 94 | 120 |
|---|---|---|---|---|---|---|
| Complete Regression (100%) | 17 | 16 | 16 | 16 | 16 | 16 |
| Partial Regression (≧80%) | 5 | 3 | 3 | 3 | 3 | 3$^e$ |
| No Response | 2 | 2 | 1$^a$ | 1 | 1$^c$ | |
| Death | 1 | | | 2$^b$ | | |
| Tumor regrowth | | | 2 | | 1$^d$ | |
| Retreatment | | | 2 | | | |
| Histology | | 1 | | | | |

$^{a,\ c}$Mice sacrificed due to increased tumor burden
$^b$1 mouse died after retreatment; 1 mouse with no palpable tumor died after 64 days survival
$^d$Secondary metastatic tumor
$^e$Fibrous tissue In vivo Results Using the MedPulser™

Preliminary experiments using MedPulser™ (apparatus of the invention) for treatment of tumor xenografts grown subcutaneously onto nude mice have shown encouraging results. Human pancreatic xenograft (Panc-4) when treated with EPT using MedPulser™ and bleomycin showed complete tumor regression in about 75% of the mice treated up to day 39 of observation. Treatment of human prostate xenografts (PC-3) has also shown about 66% complete regression of tumors. (No tumors observed up to 60 days after treatment). Both 4 and 6 needle array are effective in treatment of tumors by EPT.

Comparison of MedPulser™ 4 and 6 Needle Array for in vitro Experiments with PC-3

Experiments were carried out to compare the efficacy of 6 vs. 4 needle array with MedPulser™ on PC-3 (human prostate cell line) in vitro. Cells were suspended in RPMI media and seeded uniformly at 200,000 cells/ml. Bleomycin at $2\times10^5$M was added to the wells (for D+E− and D+E+ only). Cells were electroporated in 24 well plates using the 6-needle and 4-needle array electrodes connected to the MedPulser. The electropulse parameters were 6×99 $\mu$s, 1129 V with the 6-needle array and 4×99 $\mu$s, 848 V with the 4-needle array. The cells were transferred to 96 well plates and incubated for 20 hours at 37° C. The cell survival was determined using XTT assay which is based on metabolic conversion of XTT to formazan and is measured spectrophotometrically at 450 nm. Only the cells which are live convert XTT to formazan. The percent cell survival values are relative values calculated from the O.D. values of the sample, a control with 100% cell survival (D−E−) and control with 0% cell survival (D−E− with SDS, which lyses all cells). The cell survival data are as follows:

TABLE 3

| Treatment | Avg. % Survival | SE |
|---|---|---|
| D−E− | 100 | 3.65 (n = 6) |
| D+E− | 27.71 | 1.05 (n = 6) |
| D−E+ (4N) | 101.15 | 4.32 (n = 12) |
| D−E+ (6N) | 97.72 | 4.33 (n = 12) |
| D+E+ (4N) | 4.78 | 7.53 (n = 12) |
| D+E+ (6N) | −4.12 | 0.59 (n = 12) |

From the preliminary data obtained in the experiments, it can be concluded that statistically both 4 and 6 needles appear to be equally effective in killing the tumor cells in vitro.

EXAMPLE 2—Clinical Trials for Basal Cell Carcinomas and Melanomas

The effectiveness of bleomycin-EPT on the tumors was to be assessed by the end of the eight-week period using the same tumor response criteria as employed in Example 1.

The concentration of bleomycin administered was 5 U/1 mL. The dosages of bleomycin were administered as follows:

TABLE 4

| Tumor Size | Dose of Bleomycin |
|---|---|
| <100 mm$^3$ | 0.5 U |
| 100–150 mm$^3$ | .75 U |
| 150–500 mm$^3$ | 1.0 U |
| 500–1000 mm$^3$ | 1.5 U |
| 1000–2000 mm$^3$ | 2.0 U |
| 2000–3000 mm$^3$ | 2.5 U |
| 3000–4000 mm$^3$ | 3.0 U |
| ≧5000 mm$^3$ | 4.0 U |

Table 5, following, shows the results of the responses to treatment.

NE=no effect; less than 50% reduction in tumor volume.

PR=partial responses; 50% or greater reduction in tumor volume.

CR=complete response; disappearance of all evidence of tumor as determined by physical examination, and/or biopsy.

EXAMPLE 3—EPT for Head and Neck Cancers

All of the following patients were treated with bleomycin intratumoral injection and needle arrays of different diameters with six needles. The voltage was set to achieve a nominal electric field strength of 1300 V/cm (the needle array diameter was multiplied by 1300 to give the voltage the generator was set at). The pulse length was 100 $\mu$s.

Study Methods

The study was designed as a single center feasibility clinical study in which the efficacy of the EPT procedure in combination with intralesional bleomycin was compared to that for traditional surgery, radiation, and/or systemic chemotherapy. Approximately 50 study subjects were enrolled in the study. All study subjects were assessed prior to treatment by examination and biopsy. Postoperative assessment of study subjects was weekly for 4–6 weeks, and monthly thereafter for a total of 12 months. Approximately 8 to 12 weeks following therapy, a biopsy of the tumor site was performed. Use of CT or MRI scans was utilized in accordance to standard medical follow-up evaluation of HNC subjects.

Tumor evaluation includes measuring the tumor diameter (in centimeters) and estimating its volume (in cubic centimeters). Prior to intratumoral administration of bleomycin sulfate, the tumor site is anesthetized with 1% lidocaine (xylocaine) and 1:100,000 epinephrine. The concentration of bleomycin sulfate injected is 4 units per milliliter, up to a maximum dose of 5 units per tumor. If more than one tumor per subject is treated, a total of 20 units per subject should not be exceeded. The dose of bleomycin administered is to be 1 unit/cm$^3$ of calculated tumor volume. Approximately ten minutes subsequent to the injection of bleomycin sulfate, the applicator is placed on the tumor and electrical pulses initiated. Each application or an initiation of electrical pulses is referred to as a sequence. The use of EPT is not a contraindication to any subsequent palliative treatment required by the subject.

In this study, success was defined as significant tumor regression in a period of 16 weeks or less without major side effects seen with traditional therapy. There are three possible response outcomes:

Complete Response (CR): Disappearance of all evidence of tumor as determined by physical examination, and/or biopsy.

Partial Response (PR): 50% or greater reduction in tumor volume.

No Response (NR): less than 50% reduction in tumor volume.

If the tumor increases (25% tumor volume) in size, other therapy, if indicated, was instituted per subject's desire.

Subject's Response to Treatment

Table 6 displays the subject's response to treatment. Three subjects had a complete response (Subject No. 1, 3 and 4); four subjects have had a partial response (Subject No. 2, 6, 8 and 9); and two subjects had no response (Subject No. 5 and 7) to treatment. Three subjects died prior to reaching week 12 due to progressive disease or complications unrelated to study treatment (Subject No. 2, 5 and 7). One of the three subjects achieved a PR at week 4 (Subject No. 2). Two subjects had no previous clinical cancer treatments for their tumor prior to study enrollment (Subject No. 4 and 8). Three subjects had a tumor that was not completely accessible to the applicator component of the device and therefore received segmented treatment (Subject No. 5, 7 and 9).

Table 7 shows a summary of clinical studies using bleomycin sulfate and EPT using the apparatus of the invention, MedPulser™.

TABLE 6

Response to Bleomycin Sulfate/EPT

| Subject No./Initials | Previous Treatment | Week of Treatment | Time to Response (Week) | Response Status | Last Visit (Week) |
|---|---|---|---|---|---|
| 1/J-S | S | 0 | 2, 8 | PR, CR | 22 |
| 2/G-C | R | 0, 4 | 4 | PR | 4 |
| 3/L-O | R | 0 | 3 | CR | 16 |
| 4/G-R | None | 0, 4 | 4, 9 | PR, CR | 9 |
| 5/R-H | R | 0, 4 | na | NR** | 4 |
| 6/C-B | R | 0, 12 | 2 | PR | 12 |
| 7/C-J | S, R, C | 0 | na | NR** | 1 |
| 8/L-J | None | 0, 6 | 4 | PR | 9 |
| 9/J-T | S, R, C | 0, 7 | 7 | PR** | 7 |

TABLE 6-continued

Response to Bleomycin Sulfate/EPT (S) Surgery,
(R) Radiation,
(C) Chemotherapy;
PR—Partial Response;
CR—Complete Response;
NR—No Response;
**Segmented treatment EXAMPLE 4—Low Voltage Long Pulse Length (LVLP) EPT Conventional electrochemotherapy uses high voltages short pulse durations for treatment of tumors. The electrical field conditions of 1200–1300 V/cm and 100 $\mu$s have been found to be very effective in vitro and in vivo with anticancer drugs like bleomycin, cisplatin, peplomycin, mitomycin c and carboplatin. These results refer to in vitro and in vivo work. Although such electrical conditions are well tolerated by patients in clinical situations, such treatments will typically produce muscle twitch and occasional discomfort to patients. The sensation of discomfort is often found to be associated with individual patient's perception of pain. Often patients respond very differently under the same experimental conditions. Some of these problems could be considerably reduced by using low voltage high pulse durations for electrochemotherapy. The lowest field strength reported for in vivo gene transfer is 600 V/cm (T. Nishi et al. *Cancer Res.* 56:1050–1055, 1996). The maximum field strength used for the in vitro EPT experiments are shown in Table 8 where the field strength necessary to kill 50% of the cells is <50V/cm.

The following in vitro experiments with various tumor cell lines, such as MCF-7 (human breast cancer), PC-3 (human prostate cancer) and C6 (Rat Glioma) have shown that low voltage, long pulse durations are equal or better than high voltage short pulse durations in terms of tumor cell killing. Results are illustrated within MCF-7. Titration of pulse length has shown that it can range from 4–15 msec. The electroporation response of MCF-7 has been carried out at both high voltage/short pulse length (HVSP) and low voltage/long pulse length (LVLP) using an XTT assay after 70 hours which is based on metabolic conversion of XTT to formazan which is measured spectrophotometrically at 450 nm. (M. W. Roehm, et al., *An Improved Colorimetric Assay for Cell Proliferation and Viability Utilizing the Tetrazolium Salt XTT, J. Immunol. Methods* 142:2, 257–265, 1991.) XTT is a tetrazolium reagent, 2,3-bis(2-methoxy-4-nitro-5-sulfophenyl)-5-[(phenylamino) carbonyl]-2H-tetrazolium hydroxide (XTT), which is metabolically reduced in viable cells to a water-soluble formazan product. Therefore, only the cells which are live convert XTT to formazan. The percent cell survival values are relative values calculated using a formula from the O.D. values of the sample. (Control, with 100% cell survival (D–E) and control with 0% cell survival (D–E with SDS)). The experiments with HVSP were done to permit direct comparison with the currently developed LVLP mode of EPT.

TABLE 8

| Cell line | Cell Type | HVSP LD$_{50}$ (V/cm) | LVLP LD$_{50}$ (V/cm) |
|---|---|---|---|
| MCF-7 | Breast Cancer (Human) | 1800 | 50 |

(LD$_{50}$ is the lethal dose of pulse required to kill 50% of cells)

Voltages as low as 25 V/cm caused significant cytotoxicity to the cells. An increase in the electric field resulted in complete cell killing. Some of the cell lines like C6 glioma which were not affected very significantly by high voltage pulses but were completely killed by low voltages of 20–30 V/cm. These in vitro results clearly establish the potential of using the LVLP modality of EPT treatment.

Cytotoxicity of Drugs with EPT in vitro

Experimental results of in vitro EPT experiments with various drugs using MCF-7 both high voltage and low voltage are described below.

Cells were obtained from ATCC (American Type Tissue Collection, Rockville, Md, U.S.A.) and maintained by their recommended procedures. Cells were suspended in appropriate medium and were uniformly seeded in 24/96 well plates. One of the following drugs: bleomycin, cisplatin, mitomycin C, doxorubicin and taxol was added directly to the cell suspensions at final concentrations of about $1 \times 10^{-4}$ (1E-4) to $1.3 \times 10^{-9}$ (1.3E-9). The electrical pulse a BTX T820 electro square porator were delivered to the cell suspensions in microplates using a BTX needle array electrode as described herein. Depending on the experiment, six pulses of either 100 μs or 10 ms and at various nominal electric fields of either high voltage or low voltages were applied between two opposite pairs of a six-needle array using EPT-196 needle array switch. The microplates were incubated for either 20 hrs or 70 hrs and the cell survival was measured by the XTT assay. Some of the results are presented in FIGS. 15(a), 15(b), 16(a), 16(b) and 17.

Figure 17:
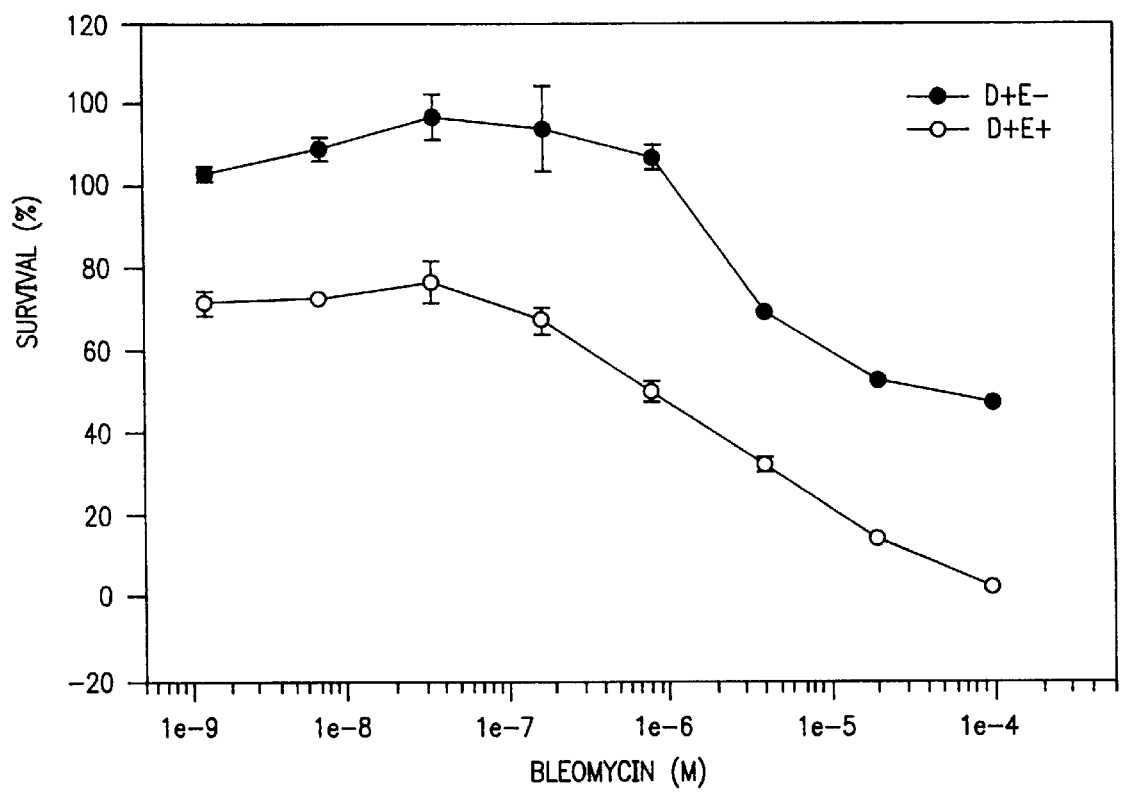
FIG. 17 shows the effect of non-pulsed and pulsed MCF-7 cells with different concentration of bleomycin and the MedPulser™.

The curves corresponding to FIG. 17 were obtained using the MedPulser™

Figure 15A:
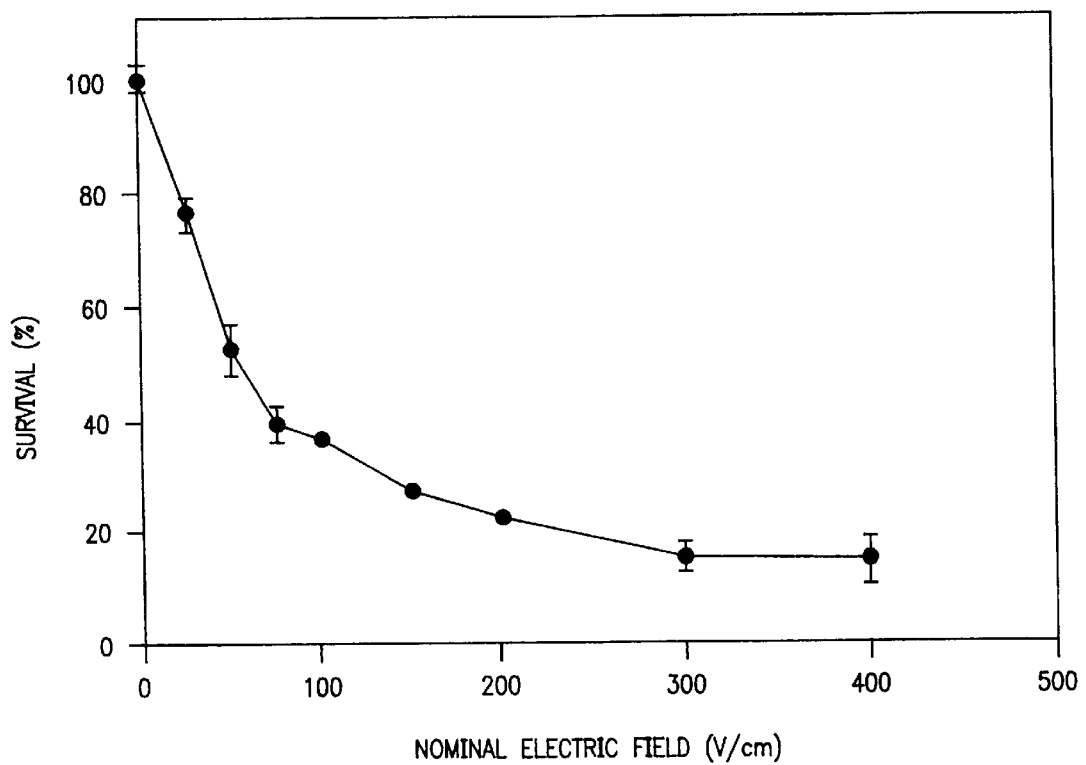
FIGS. 15a and 15b show the survival of MCF-7 (breast cancer) cells when exposed to low voltage and high voltage EPT, respectively.
Figure 15B:
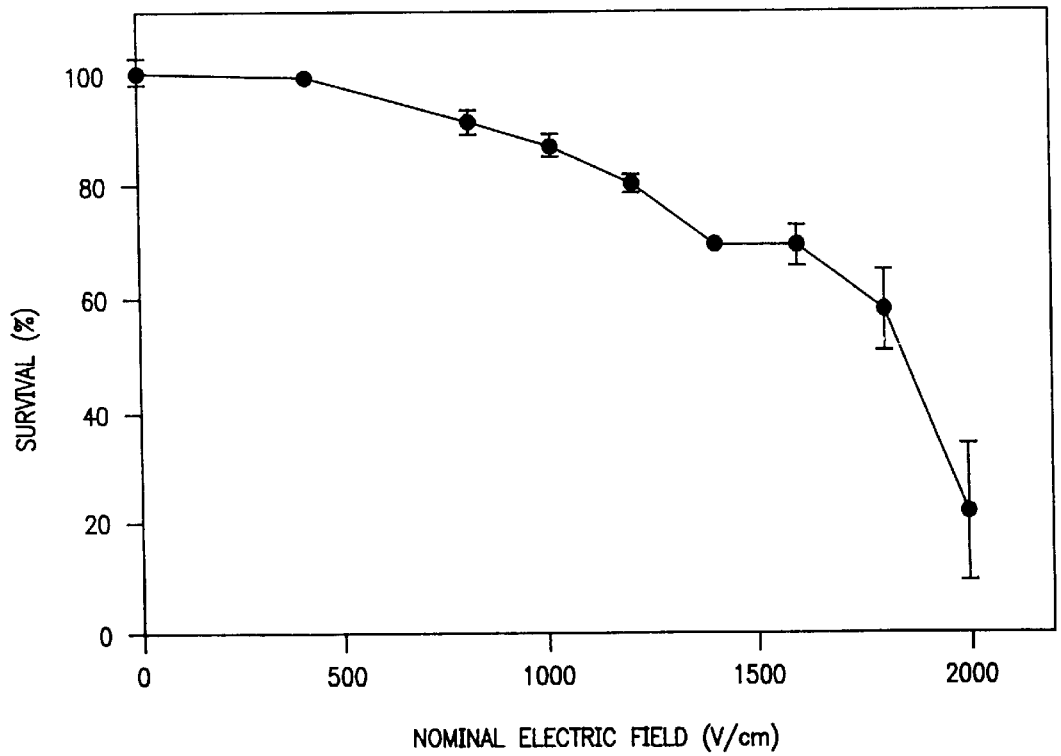
Figure 16A:
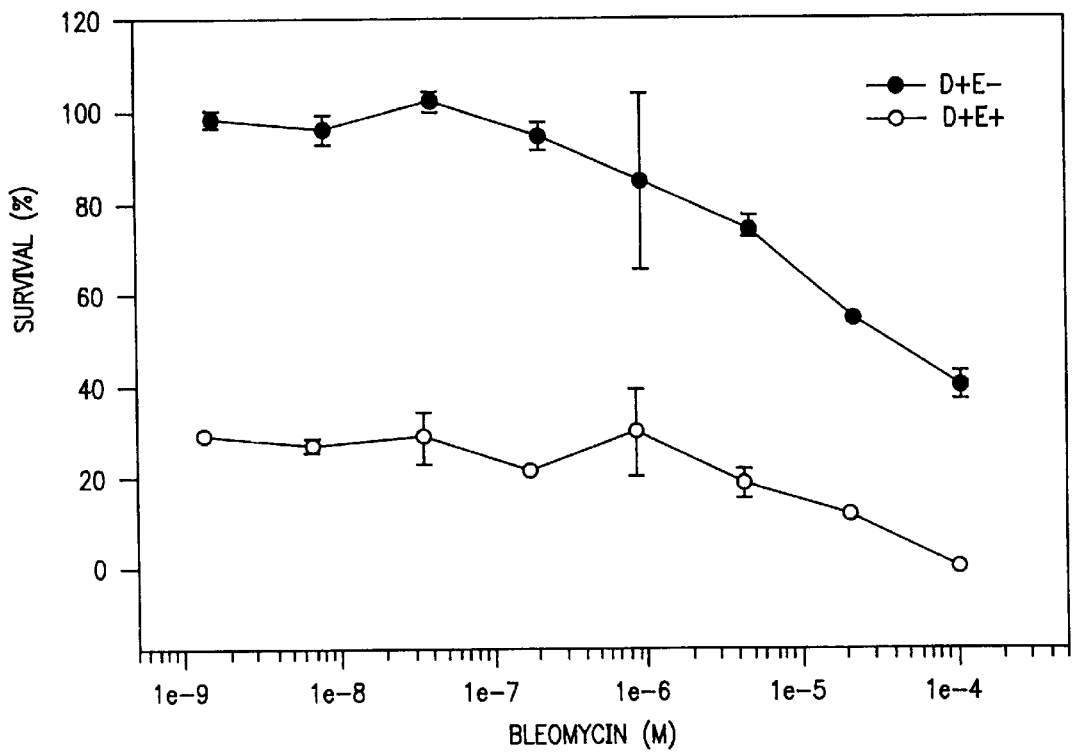
FIGS. 16a and 16b show the survival of MCF-7 cells when exposed to low voltage and high voltage EPT, respectively, with bleomycin.
Figure 16B:
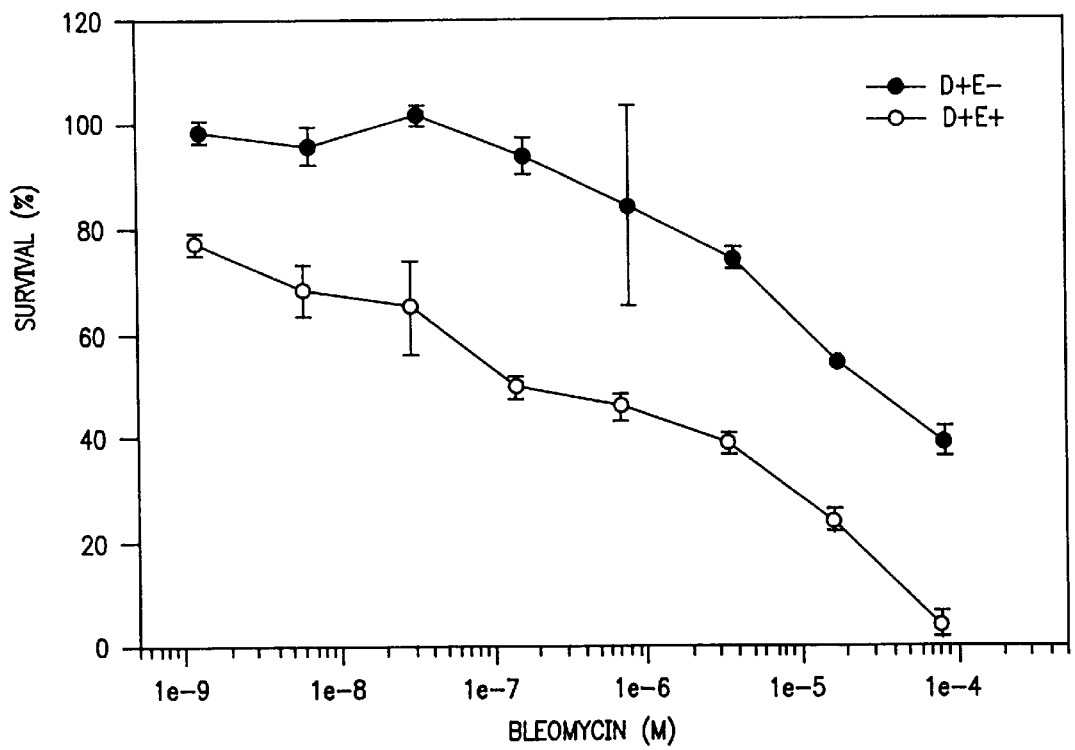

For the LVLP mode, the method shows that cell survivability is well below 50% even when the cells are pulsed in the absence of drugs; this percentage is further reduced when combined with the drugs. It is more desirable to show that the drugs show the effect rather than the pulse and requires selecting initial survival values with the pulse alone at about 80%. Typical cell killing curves for LVLP mode are shown in FIG. 15(a).

Although the invention has been described with reference to the presently preferred embodiment, it should be understood that various modifications can be made without departing from the spirit of the invention. Accordingly, the invention is limited only by the following claims.

What is claimed is:

1. A method for automatically setting an electrode needle addressing scheme for an electroporation therapy apparatus capable of accepting a plurality of electrode applicators having varying numbers of electrode needles, comprising the steps of:

(a) providing a type identification element in an electrode applicator having a number of electrode needles, the type identification element representing at least the number of such electrode needles;

(b) coupling the electrode applicator to the electroporation therapy apparatus;

(c) determining the number of electrode needles from the type identification element;

(d) setting the electroporation therapy apparatus to address the determined number of electrode needles.

2. The method of claim 1, further including the step of setting the electroporation therapy apparatus to address the determined number of electrode needles in a selected pattern.

3. A method for automatically setting electrical treatment parameters for an electroporation therapy apparatus capable of accepting a plurality of different electrode applicators, comprising the steps of:

(a) providing a type identification element in an electrode applicator, the type identification element representing at least one of the following electrical treatment parameters to be used with the electrode applicator: needle voltage setpoint, pulse length, or pulse shape;

(b) coupling the electrode applicator to the electroporation therapy apparatus;

(c) determining the electrical treatment parameters from the type identification element;

(d) setting the electroporation therapy apparatus to the determined electrical treatment parameters.

4. A system for automatically setting an electrode needle addressing scheme for an electroporation therapy apparatus capable of accepting a plurality of electrode applicators having varying numbers of electrode needles, comprising:

(a) an electrode applicator having a number of electrode needles and a type identification element, the type identification element representing at least the number of such electrode needles;

(b) a circuit in the electroporation therapy apparatus for determining the number of electrode needles from the type identification element when the electrode adapter is coupled to the electroporation therapy apparatus;

(c) a circuit for setting the electroporation therapy apparatus to address the determined number of electrode needles.

5. A system for automatically setting electrical treatment parameters for an electroporation therapy apparatus capable of accepting a plurality of different electrode applicators, comprising:

(a) an electrode applicator having a type identification element, the type identification element representing at least one of the following electrical treatment parameters to be used with the electrode applicator: needle voltage setpoint, pulse length, or pulse shape;

(b) a circuit in the electroporation therapy apparatus for determining the electrical treatment parameters from the type identification element when the electrode adapter is coupled to the electroporation therapy apparatus;

(c) a circuit for setting the electroporation therapy apparatus to the determined electrical treatment parameters.

6. An electrode applicator for automatically setting an electrode needle addressing scheme in an electroporation therapy apparatus capable of accepting a plurality of electrode applicators having varying numbers of electrode needles, comprising:

(a) a number of electrode needles configured for electroporation therapy; and (b) a type identification element, configured to be electrically coupled to the electroporation therapy apparatus, the type identification element representing at least the number of such electrode needles;

wherein the type identification element, when the electrode adapter is coupled to the electroporation therapy apparatus, provides the type identification element to the electroporation therapy apparatus and permits the electroporation therapy apparatus to automatically set itself to address the determined number of electrode needles.

7. An electrode applicator for automatically setting electrical treatment parameters for an electroporation therapy apparatus capable of accepting a plurality of different electrode applicators, comprising:

(a) a number of electroporation therapy electrode needles; and (b) a type identification element, configured to be electrically coupled to the electroporation therapy apparatus, the type identification element representing at least one of the following electrical treatment parameters to be used with the electrode applicator: needle voltage setpoint, pulse length, or pulse shape;

wherein the type identification element, when the electrode adapter is coupled to the electroporation therapy apparatus, provides the type identification element to the electroporation therapy apparatus and permits the electroporation therapy apparatus to automatically set itself to the determined electrical treatment parameters.

8. An electroporation therapy apparatus, comprising:

(a) a source for generating voltage pulses;

(b) a connector for one of a plurality of electrode applicators having varying numbers of electrode needles, each electrode applicator including a type identification element, the type identification element representing at least the number of such electrode needles;

(c) a circuit for determining a determined number of electrode needles from the type identification element when one such electrode adapter is coupled to the connector;

(d) a circuit for setting the electroporation therapy apparatus to address the determined number of electrode needles and supply generated voltage pulses to addressed electrode needles.

9. The electroporation therapy apparatus of claim 8, further including a remote therapy activation device for controlling generation of voltage pulses.

10. The electroporation therapy apparatus of claim 9, wherein the remote therapy activation device comprises a foot pedal switch.

11. An electroporation therapy apparatus, comprising:

(a) a source for generating voltage pulses having programmable electrical treatment parameters comprising at least one of: needle voltage setpoint, pulse length, or pulse shape;

(b) a connector for one of a plurality of electrode applicators having electrode needles, each electrode applicator requiring selected electrical treatment parameters, each electrode applicator including a type identification element, the type identification element representing the specific electrical treatment parameters to be used with the electrode applicator;

(c) a circuit for determining the specific electrical treatment parameters from the type identification element when an electrode adapter is coupled to the connector;

(d) a circuit for programming the electrical treatment parameters for the electroporation therapy apparatus to the determined specific electrical treatment parameters.

12. The electroporation therapy apparatus of claim 11, further including a remote therapy activation device for controlling generation of voltage pulses.

13. The electroporation therapy apparatus of claim 12, wherein the remote therapy activation device comprises a foot pedal switch.

14. An electrode applicator for automatically setting needle array type parameters for an electroporation therapy apparatus capable of accepting a plurality of different electrode applicators, comprising:

(a) a number of electroporation therapy electrode needles; and (b) a type identification element, configured to be electrically coupled to the electroporation therapy apparatus, the type identification element representing at least one of the following needle array type parameters: number of needles, needle spacing, or needle switching sequence;

wherein the type identification element, when the electrode adapter is coupled to the electroporation therapy apparatus, provides the type identification element to the electroporation therapy apparatus and permits the electroporation therapy apparatus to automatically respond to the determined needle array type parameters.

15. An electrode applicator for providing applicator specific parameters for an electroporation therapy apparatus capable of accepting a plurality of different electrode applicators, comprising:

(a) a number of electroporation therapy electrode needles; and (b) a type identification element, configured to be electrically coupled to the electroporation therapy apparatus, the type identification element providing an indication of at least one applicator specific parameter;

wherein the type identification element, when the electrode adapter is coupled to the electroporation therapy apparatus, provides the type identification element to the electroporation therapy apparatus and permits the electroporation therapy apparatus to respond to the determined applicator specific parameters.

16. The electrode applicator of claim 15, wherein at least one applicator specific parameter is the number of needles in the electrode applicator.

17. The electrode applicator of claim 15, wherein at least one applicator specific parameter is the spacing of the needles in the electrode applicator.

18. The electrode applicator of claim 15, wherein at least one applicator specific parameter is a needle switching sequence for the electrode applicator.

19. The electrode applicator of claim 15, wherein at least one applicator specific parameter is a voltage setpoint to be applied to the needles of the electrode applicator.

20. The electrode applicator of claim 15, wherein at least one applicator specific parameter is a pulse length to be applied to the needles of the electrode applicator.

21. The electrode applicator of claim 15, wherein at least one applicator specific parameter is a pulse shape to be applied to the needles of the electrode applicator.

22. The electrode applicator of claim 15, wherein at least one applicator specific parameter is a shelf life of the electrode applicator.

23. The electrode applicator of claim 15, wherein at least one applicator specific parameter is a usage limit for the electrode applicator.

24. The electrode applicator of claim 15, further including a writable active circuit which can store data specific to the electrode applicator.

25. The electrode applicator of claim 15, wherein at least one applicator specific parameter is a shelf life of the electrode applicator, and a shelf life lockout code is stored in the writable active circuit when the shelf life is exceeded.

26. The electrode applicator of claim 25, wherein at least one applicator specific parameter is a usage limit for the electrode applicator, and a usage limit lockout code is stored in the writable active circuit when the usage limit is exceeded.

27. The electrode applicator of claim 25, wherein a usage history for the electrode applicator is stored in the writable active circuit.

28. The electrode applicator of claim 25, wherein captured error codes are stored in the writable active circuit.

* * * * *

Disclaimer 6,055,453—Gunter A. Hofmann; Sukhendu B. Dev, both of San Diego; Steven C. Dimmer, Valley Center; Jeffrey I. Levatter, Rancho Santa Fe; Gurvinder S. Nanda, San Diego, all of Calif. APPARATUS FOR ADDRESSING NEEDLE ARRAY ELECTRODES FOR ELECTROPORATION THERAPY. Patent dated April 25, 2000. Disclaimer filed April 2, 2001, by the assignee, Genetronics, Inc.

Hereby enters this disclaimer to claims 8-13 of said patent.

*(Official Gazette, June 5, 2001)*